United States Patent
Samusik et al.

(10) Patent No.: US 12,338,490 B2
(45) Date of Patent: *Jun. 24, 2025

(54) MULTIPLEXED SINGLE MOLECULE RNA VISUALIZATION WITH A TWO-PROBE PROXIMITY LIGATION SYSTEM

(71) Applicant: The Board of Trustees of the Leland Stanford Junior University, Stanford, CA (US)

(72) Inventors: Nikolay Samusik, Mountain View, CA (US); Felice Alessio Bava, Menlo Park, CA (US); Yury Goltsev, Stanford, CA (US); Garry P. Nolan, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 215 days.

This patent is subject to a terminal disclaimer.

(21) Appl. No.: 17/230,706

(22) Filed: Apr. 14, 2021

(65) Prior Publication Data
US 2021/0238665 A1   Aug. 5, 2021

Related U.S. Application Data

(63) Continuation of application No. 16/079,017, filed as application No. PCT/US2017/019443 on Feb. 24, 2017, now Pat. No. 11,008,608.
(Continued)

(51) Int. Cl.
C12P 19/34   (2006.01)
C12Q 1/682   (2018.01)
(Continued)

(52) U.S. Cl.
CPC .......... *C12Q 1/6841* (2013.01); *C12Q 1/682* (2013.01); *G01N 33/542* (2013.01);
(Continued)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS 6,235,502 B1   5/2001   Weissman et al.
6,316,229 B1   11/2001   Lizardi et al.
(Continued)

FOREIGN PATENT DOCUMENTS

JP   2014506472   3/2014
WO   WO2001/061037   8/2001
(Continued)

OTHER PUBLICATIONS

"Mass cytometry" from Wikipedia. Printed on Dec. 13, 2023.*
(Continued)

*Primary Examiner* — Frank W Lu
(74) *Attorney, Agent, or Firm* — Pamela J. Sherwood; Bozicevic, Field & Francis LLP

(57) ABSTRACT

SNAIL provides cost-efficient detection of specific nucleic acids in single cells, and may be combined with flow cytometry to simultaneously analyze large numbers of cells for a plurality of nucleic acids, e.g. at least one, to up to 5, up to 10, up to 15, up to 20 or more transcripts can be simultaneously analyzed, at a rate of up to about 50, 100, 250, 500 or more cells/second. The methods require only two primers for amplification, and may further include a detection primer.

14 Claims, 14 Drawing Sheets

Specification includes a Sequence Listing.

Related U.S. Application Data

(60) Provisional application No. 62/300,596, filed on Feb. 26, 2016.

(51) Int. Cl.
  *C12Q 1/6841* (2018.01)
  *G01N 33/542* (2006.01)

(52) U.S. Cl.
  CPC .  *C12Q 2525/307* (2013.01); *C12Q 2531/125* (2013.01); *C12Q 2533/107* (2013.01); *C12Q 2543/10* (2013.01); *C12Q 2600/16* (2013.01)

(56) References Cited

U.S. PATENT DOCUMENTS

| | | | |
|---|---|---|---|
| 6,558,928 | B1 | 5/2003 | Landegren et al. |
| 8,497,069 | B2 | 7/2013 | Hutchison, III et al. |
| 11,008,608 | B2 * | 5/2021 | Samusik .............. G01N 33/542 |
| 2005/0112639 | A1 | 5/2005 | Wang et al. |
| 2012/0003657 | A1 | 1/2012 | Myllykangas et al. |
| 2014/0170654 | A1 | 6/2014 | Landegren et al. |
| 2015/0377886 | A1 | 12/2015 | Ciceri et al. |

FOREIGN PATENT DOCUMENTS

| | | |
|---|---|---|
| WO | WO2012110899 | 8/2012 |
| WO | WO2012/160083 | 11/2012 |
| WO | WO2013/173774 | 11/2013 |

OTHER PUBLICATIONS

Larsson et al. (2010) "In situ detection and genotyping of individual mRNA molecules", Nature Methods, pp. 395-397, (7), Nature, London, United Kingdom.

Player et al. (2001) "Single-copy gene detection using branched DNA (bDNA) in situ hybridization", J. Histochem. Cytochem, pp. 603-612, vol. 49, Issue 5, The Histochemical Society, Inc., Bethesda, MD.

Porichis et al. (2014) "High-throughput detection of miRNAs and gene-specific mRNA at the single-cell level by flow cytometry", Nature Communications, pp. 1-24 5, 5641, Springer, Berlin, Germany.

Bendall et al. (2011) "Single-cell mass cytometry of differential immune and drug responses across a human hematopoietic continuum", Science, pp. 687-696, vol. 332, Issue 6030, American Association for the Advancement of Science, Washington, D.C.

Wolf-Yadlin et al. (2006) "Effects of HER2 overexpression on cell signaling networks governing proliferation and migration", Mol Syst Biol, vol. 2, Issue 1, Nature, London, United Kingdom.

Angelo et al. (2014) "Multiplexed ion beam imaging (MIBI) of human breast tumors", Nat Med. pp. 436-442, 20(4), Springer, Berlin, Germany.

Fredriksson et al. (2002) "Protein detection using proximity-dependent DNA ligation assays", Nat Biotechnol, pp. 473-477, 20, Springer, Berlin, Germany.

Soderberg et al., (2006) "Direct observation of individual endogenous protein complexes in situ by proximity ligation", Nat. Methods, pp. 995-1000, vol. 3, No. 12, Nature, London, United Kingdom.

Lee et al. (2015) "Fluorescent in situ sequencing (FISSEQ) of RNA for gene expression profiling in intact cells and tissues" pp. 442-458.

Lee et al. (2014) : "Highly Multiplexed Subcellular RNA Sequencing in Situ" pp. 1360-1363.

Wang et al. (2018) "Three-dimensional intact-tissue sequencing of single-cell transcriptional states" p. eaat5691.

Weibrecht et al. (2013) "In situ detection of individual mRNA molecules and protein complexes or post-translational modifications using padlock probes combined with the in situ proximity ligation assay.", Nature Protocols, vol. 8, No. 2, pp. 355-372.

Flow cytometry from Wikipedia. Printed on Jul. 6, 2020.

Millard et al., (2006) "Detection of infectious haematopoietic necrosis virus and infectious salmon anameia virus by molecular padlock amplification." Journal of Fish Diseases, vol. 29, pp. 201-213.

* cited by examiner

NALM-6

Jurkat

Cluster ID cMyc

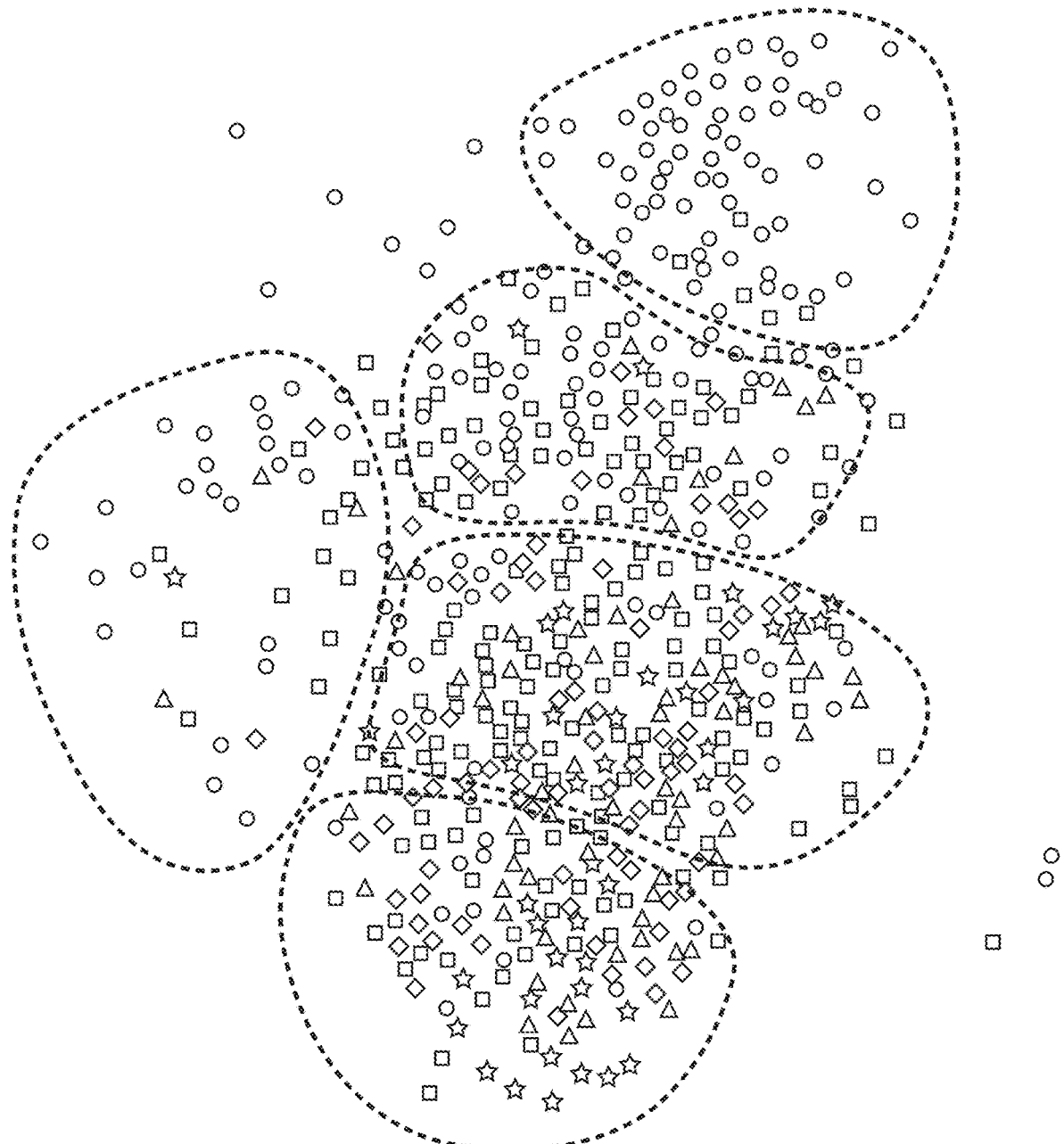

Ki67

MYCN

WFDC2

PBOV1

MUC16

E-cadherin

MULTIPLEXED SINGLE MOLECULE RNA VISUALIZATION WITH A TWO-PROBE PROXIMITY LIGATION SYSTEM

CROSS REFERENCE

This application is a continuation and claims benefit of 371 application Ser. No. 16/079,017, filed Aug. 22, 2018, now U.S. Pat. No. 11,008,608, issued May 18, 2021, and claims benefit of PCT Application No. PCT/US2017/019443, filed Feb. 24, 2017, which claims benefit of U.S. Provisional Patent Application No. 62/300,596, filed Feb. 26, 2016, which applications are incorporated herein by reference in their entirety.

FEDERALLY SPONSORED RESEARCH AND DEVELOPMENT

This invention was made with Government support under contract HHSF223201210194C awarded by the Food and Drug Administration and under contract A1100627 awarded by the National Institutes of Health. The Government has certain rights in the invention.

BACKGROUND OF THE INVENTION

Studying the mechanisms of gene expression regulation is necessary to understand how their dysregulation can lead to disease states. Spatial distribution of messenger RNAs (mRNAs) is tightly regulated both at the cellular and tissue levels. Analyzing both the abundance and the spatial distribution of mRNAs is often limited by either the number of fluorophores that can be simultaneously detected by a conventional microscope or by laborious, time consuming and expensive methods. Detection of specific mRNA molecules in single cells usually involves production of cDNA, for example the FISSEQ technique, or padlock probe ligation on cDNA followed by rolling circle amplification, whereby the sensitivity is limited by the low efficiency of reverse transcriptase.

Alternatively, single molecule RNA detection can utilize hybridization of multiple short fluorescently labelled nucleotide probes directly to the target mRNA, for example single molecule RNA-FISH. These methods have a disadvantage that multiple probes must be synthesized; and such probes generally need to be targeted to open reading frames.

Most recently, we published a proximity-based RNA detection technique PLAYR, which enabled single-cell RNA detection on CyTOF. The problem is, however, that PLAYR involves a complex four-probe system that requires two-step hybridization and features intermediate hybridization specificity sequences that complicate the probe design process. Additionally, each gene requires a different intermediate hybridization sequence, and each new sequence has to be tested independently to ensure the efficiency of ligation and lack of cross-talk, which makes the design of highly multiplexed experiments a laborious task.

High-throughput measurements of gene expression using microarray technology or high throughput sequencing contribute tremendously to our understanding of how genetic networks coordinately function in normal cells and tissues and how they malfunction in disease. Such measurements allow one to infer the function of genes based on their expression patterns, to detect which genes have altered expression in disease, and to identify expression signatures that are predictive of disease progression. However, bulk transcriptome measurements only inform on the average gene expression in a sample. Thus, in a complex sample containing several cell types with different gene expression signatures, only the most abundant signature but not necessarily the most meaningful will be captured. Accordingly, the variability in single-cell gene expression in most biological systems and especially in tissues and tumors generates a need for techniques aimed at characterizing gene expression programs in individual cells of interest.

The increasing appreciation for the importance of single-cell measurements is reflected in the vast number of single-cell analysis platforms that have been successfully commercialized in recent years, including mass cytometry and microfluidic-based approaches. While flow cytometry provides an excellent platform for the detection of proteins in single cells using antibodies, no comparable solution exists for the detection of nucleic acids. Microfluidic technologies for the detection and quantification of mRNA in single cells are very costly and their throughput is several orders of magnitude lower compared with what can be achieved for proteins using flow cytometry.

To overcome the limitations of bulk analyses, a number of technologies have been developed that measure gene expression in single cells. In one such method, up to 20 short oligonucleotide probe pairs hybridize in adjacent positions to a target RNA. These binding events are subsequently amplified using branched DNA technology, where the addition of sets of oligonucleotides in subsequent hybridization steps gives rise to a branched DNA molecule. The presence of such a branched DNA structure can then be detected and quantified by flow cytometry using a fluorescent probe. This technology enables the detection of only few RNA copy numbers in millions of single cells but is currently limited to the simultaneous detection of small numbers of measured transcripts. Furthermore, the protocol is long and laborious and the buffers used are not compatible with some fluorophores commonly used in flow cytometry and cannot be used at all in mass cytometry.

Another method (Larsson et al. (2010) Nature Methods), uses padlock probes, i.e. linear probes that can be converted into a circular DNA molecule by target-dependent ligation upon hybridization to a target RNA molecule. The resulting circularized single-stranded DNA probe can then be amplified using the enzyme phi29 polymerase in a process termed Rolling Circle Amplification (RCA). This process produces a single-stranded DNA molecule containing hundreds of complementary tandem repeats of the original DNA circle. This RCA product can be made visible through the addition of fluorescently labeled detection probes that will hybridize to a detection sequence in the product. This technology enables the multiplex detection of transcripts but requires reverse transcription of target mRNAs using specific primers and RNAse H digestion of the original transcript before hybridization of the padlock probe. Therefore, it introduces additional variability in the assay and requires the design and optimization of both probes and primers.

Another commercially available solution for single-cell mRNA measurements is based on the physical separation of single cells using a microfluidic device followed by library preparation and sequencing. This is currently the only genome-wide solution but the very limited throughput (96 cells per run) makes it unsuitable for the analysis of samples with multiple cell populations such as blood samples or tumors. Additionally, the technology is expensive compared to the other approaches, and does not allow for the simultaneous detection of proteins and mRNAs in the same cell.

There is a need for methods that can provide information on multiple transcripts in single cells, particularly that can be usefully combined with protein analysis. Such methods can help analyze how biological networks coordinately function in normal and diseased cells and tissues. The present invention addresses this need.

PUBLICATIONS

Larsson et al. In situ detection and genotyping of individual mRNA molecules. Nat. Methods 7, 395-397 (2010). Player et al. Single-copy gene detection using branched DNA (bDNA) in situ hybridization. J. Histochem. Cytochem. 49, 603-612 (2001). Porichis, F. et al. High-throughput detection of miRNAs and gene-specific mRNA at the single-cell level by flow cytometry. Nature Communications 5, 5641 (2014). Bendall, S. C. et al. Single-cell mass cytometry of differential immune and drug responses across a human hematopoietic continuum. Science 332, 687-696 (2011). Wolf-Yadlin, A. et al. Effects of HER2 overexpression on cell signaling networks governing proliferation and migration. Mol Syst Biol 2, 54 (2006). Angelo, M. et al. Multiplexed ion beam imaging of human breast tumors. Nat Med 20, 436-442 (2014). Fredriksson, S. et al. Protein detection using proximity-dependent DNA ligation assays. Nat Biotechnol 20, 473-477 (2002). Söderberg, O. et al. Direct observation of individual endogenous protein complexes in situ by proximity ligation. Nat. Methods 3, 995-1000 (2006).

International patent applications WO2012/160083; WO2001/061037; WO2013/173774.

SUMMARY OF THE INVENTION

Compositions and methods are provided for the analysis of mRNA species at a single cell level. The methods of the invention may be referred to as SNAIL-RCA, which stands for Splint Nucleotide Assisted Intramolecular Ligation followed by lolling Circle Amplification. In the methods of the invention, mRNA present in a cell of interest serves as a scaffold for an assembly of a complex that comprises two oligonucleotides, referred to herein as Splint Primer Oligonucleotide (SPO) and Padlock Oligonucleotide (PO). In some embodiments the amplification reaction mixture comprises, consists or consists essentially of two probes for each target sequence, and the method can be performed in the absence of additional probes for a given target sequence.

Each of SPO and PO comprise a first complementarity region (CR1 and CR1', respectively) that are complementary to adjacent sequences on the target mRNA.

Each of SPO and PO further comprise a second complementarity region (CR2 and CR2') located adjacent to CR1 or CR1'. CR2', which is present on PO, is a split region, where the 5' and the 3' ends of PO hybridize to CR2 in a butt head-to-end fashion, such that after the hybridization the 5' and the 3' ends of PO are positioned directly adjacent to one another. A schematic is shown in FIG. 1. PO may further comprise a spacer region, which in the circular form of the molecule is between CR1' and CR2'. In the linear form of PO, the 5' terminus is phosphorylated, so that upon annealing of both ends to CR2, the oligonucleotide can be circularized by ligation, using any suitable DNA ligase enzyme, e.g. T4 DNA ligase.

In an alternative embodiment, the PO is a closed circular molecule, and the ligation step is omitted.

Upon the circularization, the PO sequence can be amplified by means of rolling circle amplification, using any strand-displacing polymerase, e.g. bacteriophage φ29 polymerase. Amplification requires a circular molecule, which in turn requires that the SPO and PO hybridize to directly adjacent regions of the same mRNA molecule and that the ligase successfully joins the 5' and 3' ends of the PO. A high level of specificity results from the requirement that both probes hybridize to adjacent locations for the amplification reaction to take place, resulting in excellent specificity, low background, and high signal-to-noise ratios.

RCA product can be detected by various methods, which include, without limitation, hybridization to a sequence specific detection oligonucleotide (DO), also referred to as a detection probe. In some embodiments the DO is conjugated to a detectable label, e.g. fluorophore, lanthanide, biotin, radionuclide, etc., where the label may be detectable by optical microscopy, SIMS ion beam imaging, etc. In some embodiments the DO is unlabeled, where the presence of the DO can be detected in a polymerization reaction primed by the DO, and where the polymerization reaction may comprise one or more dNTP comprising a detectable label. Such polymerization products may further comprise a step of adding a label, detecting a label, and removing the label for sequential detection of different products. The detection primer can be specific for a region of the RCA amplification product that is specific for the target gene, e.g. the CR1' sequence, or can be a universal detection probe that binds to a non-target specific region on the PO, e.g. the spacer region.

The methods of the invention provide advantages in the small number of probes required, which reduces the cost of analysis; and allows a high degree of multiplexing. The methods of the invention enable cost-efficient detection of specific nucleic acids in single cells, and may be combined with flow cytometry or mass cytometry to simultaneously analyze large numbers of cells for a plurality of nucleic acids, e.g. at least one, to up to 5, up to 10, up to 15, up to 20, up to 30, up to 40 or more transcripts can be simultaneously analyzed, at a rate of up to about 50, 100, 250, 500, up to 750, up to 1000 or more cells/second. An advantage of SNAIL includes the ability to simultaneously analyze multiple nucleic acids and proteins in single cells, as the method is compatible with conventional antibody staining for proteins, intracellular phosphorylation sites, and other cellular antigens. This enables the simultaneous detection of multiple nucleic acid molecules in combination with additional cellular parameters. It can be combined with various different platforms, including without limitation FACS, mass cytometry, microscopy, scanning mass spectrometry (including, but not limited to nano-SIMS), and the like.

In some embodiments, a method is provided for determining the abundance of a target nucleic acid in a single cell, the method comprising contacting a fixed and permeabilized cell with at least one pair of oligonucleotide primers under conditions permissive for specific hybridization, wherein each oligonucleotide pair comprises an SPO probe and a PO probe as described above; washing the cells free of unbound primers; performing a ligation reaction, in which PO probes, is suitably hybridized to the splint (SPO) are ligated to generate a circle; amplifying the ligated backbone/insert circle by rolling circle amplification; washing the cells free of polymerase; hybridizing detection primers to the amplified circle; washing the cells free of unbound detection probes, and quantitating the level of bound detection primers to determine the abundance of the target nucleic acid. In many embodiments, a plurality of target nucleic acids is simultaneously analyzed.

In some embodiments of the invention, SNAIL is used in combination with cytometry gating on specific cell populations, as defined by other cellular parameters measured simultaneously, for example in combination with antibody staining and mass cytometry or FACS to define a subpopulation of interest. In such embodiments, a complex cell population may be analyzed, e.g. a biopsy or blood sample potentially including immune cells, progenitor or stem cells, cancer cells, etc. For example, a method is provided for determining the abundance of one or more target nucleic acids in a defined cell type within a complex cell population, where the quantification of detection probes is combined with detection of cellular markers, including without limitation protein markers, that serve to define the cell type of interest.

In other embodiments, the methods of the invention are used for multiplexed detection and quantification of specific splice variants of mRNA transcripts in single cells.

In yet another embodiment, the methods of the invention are combined with Proximity Ligation Assay (PLA) for the simultaneous detection and quantification of nucleic acid molecules and protein-protein interactions.

With prior denaturation of endogenous cellular DNA (by heat, enzymatic methods, or any other suitable procedure), the technology is modified for the detection of specific DNA sequences (genotyping of single cells). In this adaptation, the technology enables the quantification of gene copy number variations as well as the detection of genomic translocation/fusion events. For example, in the detection of a fusion event, if a first gene is fused to a second gene the SNAIL method can be adapted, where primers can be targeted to gene 1, with the SPO sequence; and a PO probe targeted to gene 2. A signal is obtained only when the fusion transcript is present, as the individual probes do not give rise to an amplification product. A plurality of individual primers may be designed for each of gene 1 and gene 2, e.g. 2, 3, 4, 5, 6 or more.

In some embodiments, the SNAIL oligonucleotide probes are selected in part based on the Tm of the individual binding probes, or pairing probes, to minimize the chance the probes will enable "ligation" in solution. By relying on the "local concentration" increase due to proximity, a smaller number of probes pairing around the ligation point is possible.

In some embodiments the detection probe is removed after detection, or used differentially to visualize different rolling circle products at different times.

In some embodiments, binding events by the probes not an adjacent regions is detected, e.g. regions on the termini of an RNA molecule, because due to spatial 3D changes the regions come together.

In some embodiments, multiple SNAIL oligonucleotide probe pairs are simultaneously tiled across a target sequence. In some such embodiments the tiled oligonucleotides are coded to determine which is being read out.

BRIEF DESCRIPTION OF THE DRAWINGS

FIG. 4A-4J. (FIG. 4A) Co-expression of genes quantified over 602 OVCAR-4 cells. (FIG. 4B-4J) single-cell force directed layout of OVCAR cells, where edges represent correlated single-cell expression profiles computed over the panel of 24 genes. Codes represent phenotypic populations of cells identified by clustering and expression of individual genes.

DETAILED DESCRIPTION OF THE EMBODIMENTS

Figure 1A:
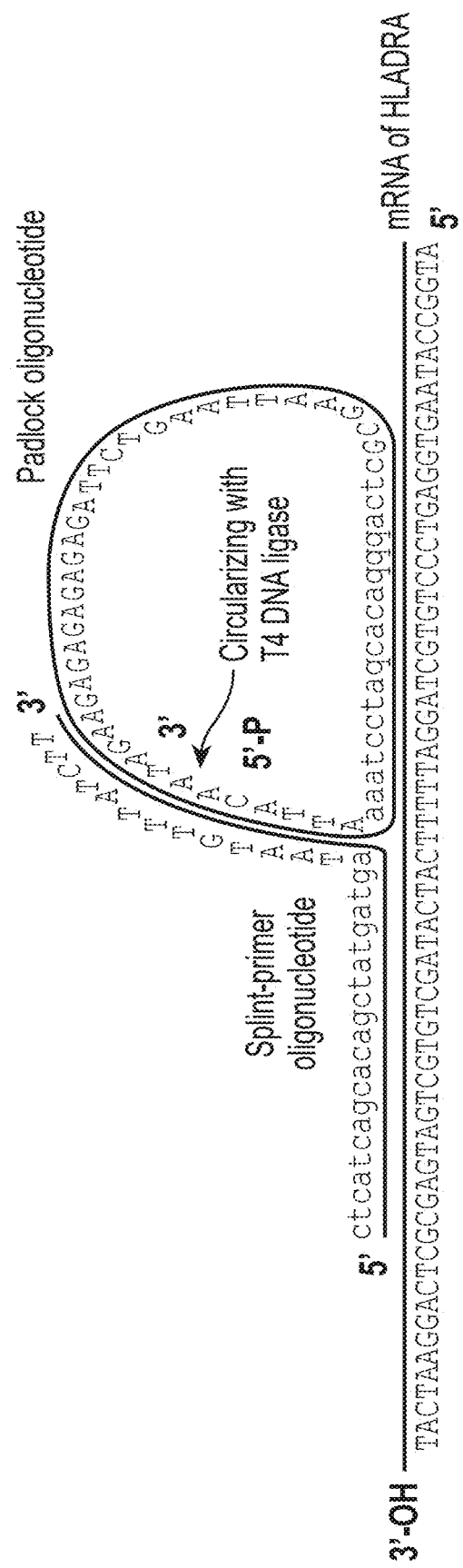
FIG. 1A-1B Steps of SNAIL-RCA protocol: hybridization, ligation, rolling circle amplification, amplification product detection. SEQ NO. 1 is the splint-primer nucleotide sequence in FIG. 1A. SEQ NO. 2 is the padlock nucleotide sequence in FIG. 1A. SEQ NO. 3 is HLADR mRNA. SEQ NOs. 4 and 5 are the nucleotides from FIG. 1B.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Target nucleic acid. As used herein, a target nucleic acid is any polynucleotide nucleic acid molecule (e.g., DNA molecule; RNA molecule, modified nucleic acid, etc.) present in a single cell. In some embodiments, the target nucleic acid is a coding RNA (e.g., mRNA). In some embodiments, the target nucleic acid is a non-coding RNA (e.g., tRNA, rRNA, microRNA (miRNA), mature miRNA, immature miRNA; etc). In some embodiments, the target nucleic acid is a splice variant of an RNA molecule (e.g., mRNA, pre-mRNA, etc.) in the context of a cell. A suitable target nucleic acid can therefore be an unspliced RNA (e.g., pre-mRNA, mRNA), a partially spliced RNA, or a fully spliced RNA, etc.

Target nucleic acids of interest may be variably expressed, i.e. have a differing abundance, within a cell population, wherein the methods of the invention allow profiling and comparison of the expression levels of nucleic acids, including without limitation RNA transcripts, in individual cells.

A target nucleic acid can also be a DNA molecule, e.g. a denatured genomic, viral, plasmid, etc. For example the methods can be used to detect copy number variants, e.g. in a cancer cell population in which a target nucleic acid is present at different abundance in the genome of cells in the population; a virus-infected cells to determine the virus load and kinetics, and the like.

Figure 1B:
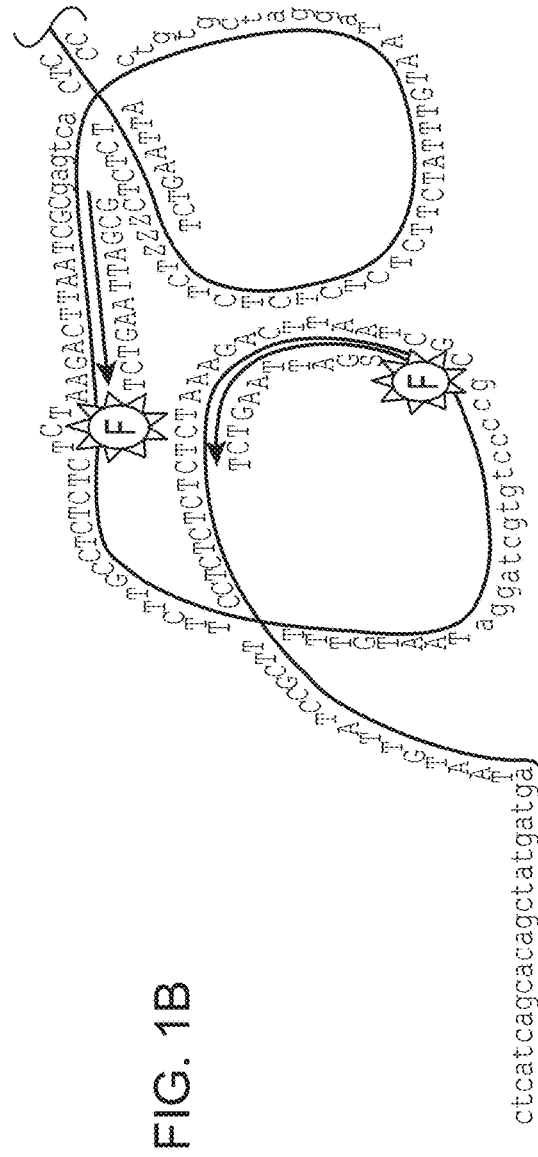
Figure 1B:
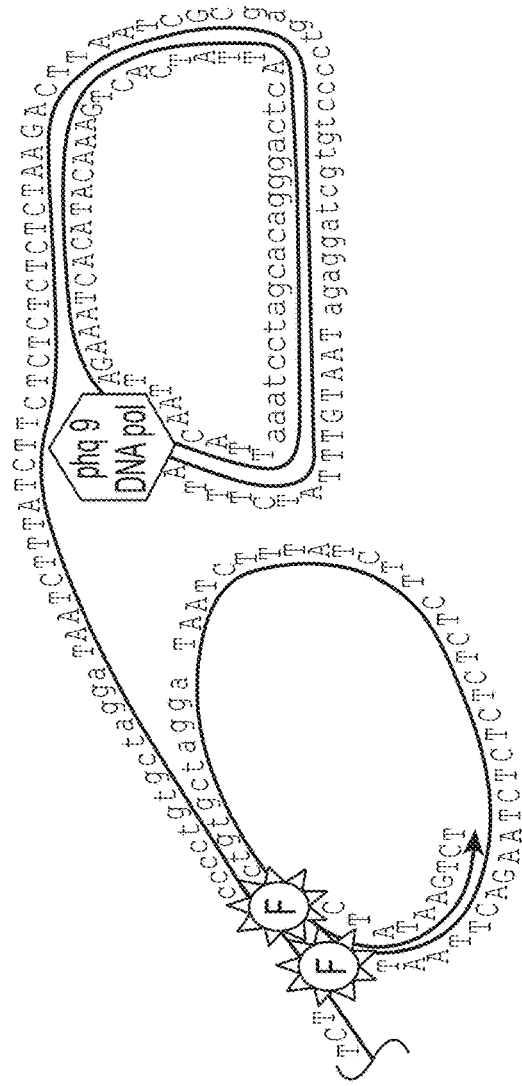

Target specific oligonucleotide primer pairs. In the methods of the invention, one or more pairs of target specific oligonucleotide primers are contacted with a cell comprising target nucleic acids. Each oligonucleotide pair comprises two oligonucleotides, referred to herein as Splint Primer Oligonucleotide (SPO) and Padlock Oligonucleotide (PO). Each of SPO and PO comprise a first complementarity region (CR1 and CR1', respectively) that are complementary to adjacent sequences on the target mRNA. Each of SPO and PO further comprise a second complementarity region (CR2 and CR2') located adjacent to CR1 or CR1'. CR2', which is present on PO, is a split region, where the 5' and the 3' ends of PO hybridize to CR2 in a butt head-to-end fashion, such that after the hybridization the 5' and the 3' ends of PO are positioned directly adjacent to one another. A schematic is shown in FIG. 1. PO may further comprise a spacer region, which in the circular form of the molecule is between CR1' and CR2'. The spacer sequence can be chosen to provide bar-coding information, etc. In the linear form of PO, the 5' terminus is phosphorylated, so that upon annealing of both ends to CR2, the oligonucleotide can be circularized by ligation, using any suitable DNA ligase enzyme, e.g. T4 DNA ligase.

A plurality of oligonucleotide pairs can be used in a reaction, where one or more pairs specifically bind to each target nucleic acid. For example, two primer pairs can be used for one target nucleic acid in order to improve sensitivity and reduce variability. It is also of interest to detect a plurality of different target nucleic acids in a cell, e.g. detecting up to 2, up to 3, up to 4, up to 5, up to 6, up to 7, up to 8, up to 9, up to 10, up to 12, up to 15, up to 18, up to 20, up to 25, up to 30, up to 40 or more distinct target nucleic acids. The primers are typically denatured prior to use, typically by heating to a temperature of at least about 50° C., at least about 60° C., at least about 70° C., at least about 80° C., and up to about 99° C., up to about 95° C., up to about 90° C.

The target binding site binds to a region of the target nucleic acid. In a pair, each target site is different, and the pair are complementary adjacent sites on the target nucleic acid, e.g. usually not more than 10 nt distant, not more than 9, 8, 7, 6, 5, 4, 3, 2, or 1 nt. distant from the other site, and may be contiguous sites. Target sites are typically present on the same strand of the target nucleic acid in the same orientation. Target sites are also selected to provide a unique binding site, relative to other nucleic acids present in the cell. Each target site is generally from about 18 to about 25 nt in length, e.g. from about 18 to 23, from about 18-21, etc. The pair of oligonucleotide probes are selected such that each probe in the pair has a similar melting temperature for binding to its cognate target site, e.g. the Tm may be from about 50° C., from about 52° C., from about 55° C., and up to about 70° C., up to about 72° C., up to about 70° C., up to about 65° C., up to about 62° C., and may be from about 58° to about 62° C. The GC content of the target site is generally selected to be no more than about 20%, no more than about 30%, no more than about 40%, no more than about 50%, no more than about 60%, no more than about 70%.

Ligase. The term "ligase" as used herein refers to an enzyme that is commonly used to join polynucleotides together or to join the ends of a single polynucleotide. Ligases include ATP-dependent double-strand polynucleotide ligases, NAD+-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases include bacterial ligases such as *E. coli* DNA ligase and Taq DNA ligase, Ampligase® thermostable DNA ligase (Epicentre®Technologies Corp., part of Illumina®, Madison, Wis.) and phage ligases such as T3 DNA ligase, T4 DNA ligase and T7 DNA ligase and mutants thereof.

Rolling Circle Amplification. A single-stranded, circular polynucleotide template is formed by ligation of the PO, which circular polynucleotide comprises a region that is complementary to the SPO probe. Upon addition of a DNA polymerase in the presence of appropriate dNTP precursors and other cofactors, the SPO probe is elongated by replication of multiple copies of the template. This amplification product can be readily detected by binding to a detection probe.

Techniques for rolling circle amplification are known in the art (see, e.g., Baner et al, Nucleic Acids Research, 26:5073-5078, 1998; Lizardi et al, Nature Genetics 19:226, 1998; Schweitzer et al. Proc. Natl Acad. Sci. USA 97:10113-119, 2000; Faruqi et al, BMC Genomics 2:4, 2000; Nallur et al, Nucl. Acids Res. 29:e1 18, 2001; Dean et al. Genome Res. 11:1095-1099, 2001; Schweitzer et al, Nature Biotech. 20:359-365, 2002; U.S. Pat. Nos. 6,054,274, 6,291,187, 6,323,009, 6,344,329 and 6,368,801). In some embodiments the polymerase is phi29 DNA polymerase.

Detection probe (DO). The presence and quantitation of an amplified SNAIL padlock sequence in a cell may be determined by contacting the cell with an oligonucleotide probe under conditions in which the probe binds to the amplified product. The probe comprises a detectable label, that can be measured and quantitated. As an alternative, the methods set forth in WO 2015/200139, herein specifically incorporated by reference, can be used.

A labeled nucleic acid probe is a nucleic acid that is labeled with any label moiety. In some embodiments, the nucleic acid detection agent is a single labeled molecule (i.e., a labeled nucleic acid probe) that specifically binds to the amplification product. In some embodiments, the nucleic acid detection agent includes multiple molecules, one of which specifically binds to the amplification product. In such embodiments, when a labeled nucleic acid probe is present, the labeled nucleic acid probe does not specifically bind to the target nucleic acid, but instead specifically binds to one of the other molecules of the nucleic acid detection agent. A hybridization probe can be any convenient length that provides for specific binding, e.g. it may be from about 16 to about 50 nt. in length, and more usually is from about 18 nt. to about 30 nt. length.

A "label" or "label moiety" for a nucleic acid probe is any moiety that provides for signal detection and may vary widely depending on the particular nature of the assay. Label moieties of interest include both directly and indirectly detectable labels. Suitable labels for use in the methods described herein include any moiety that is indirectly or directly detectable by spectroscopic, photochemical, biochemical, immunochemical, electrical, optical, chemical, or other means. For example, suitable labels include antigenic labels (e.g., digoxigenin (DIG), fluorescein, dinitrophenol (DNP), etc.), biotin for staining with labeled streptavidin conjugate, a fluorescent dye (e.g., fluorescein, Texas red, rhodamine, a fluorophore label such as an ALEXA FLUOR® label, and the like), a radiolabel (e.g., $^3$H, $^{125}$I, $^{35}$S, $^{14}$C, or $^{32}$P), an enzyme (e.g., peroxidase, alkaline phosphatase, galactosidase, and others commonly used in an ELISA), a fluorescent protein (e.g., green fluorescent protein, red fluorescent protein, yellow fluorescent protein, and the like), a synthetic polymer chelating a metal, a colorimetric label, and the like. An antigenic label can be incorporated into the nucleic acid on any nucleotide (e.g., A,U, G,C).

Fluorescent labels can be detected using a photodetector (e.g., in a flow cytometer) to detect emitted light. Enzymatic labels are typically detected by providing the enzyme with a substrate and detecting the reaction product produced by the action of the enzyme on the substrate, colorimetric labels can be detected by simply visualizing the colored label, and antigenic labels can be detected by providing an antibody (or a binding fragment thereof) that specifically binds to the antigenic label. An antibody that specifically binds to an antigenic label can be directly or indirectly detectable. For example, the antibody can be conjugated to a label moiety (e.g., a fluorophore) that provides the signal (e.g., fluorescence); the antibody can be conjugated to an enzyme (e.g., peroxidase, alkaline phosphatase, etc.) that produces a detectable product (e.g., fluorescent product) when provided with an appropriate substrate (e.g., fluorescent-tyramide, FastRed, etc.); etc.

Metal labels (e.g., $Sm^{152}$, $Tb^{159}$, $Er^{170}$, $Nd^{146}$, $Nd^{142}$, and the like) can be detected (e.g., the amount of label can be measured) using any convenient method, including, for example, nano-SIMS, by mass cytometry (see, for example: U.S. Pat. No. 7,479,630; Wang et al. (2012) Cytometry A. 2012 July; 81(7):567-75; Bandura et. al., Anal Chem. 2009 Aug. 15; 81(16):6813-22; and Ornatsky et. al., J Immunol Methods. 2010 Sep. 30; 361(1-2):1-20. As described above, mass cytometry is a real-time quantitative analytical technique whereby cells or particles are individually introduced into a mass spectrometer (e.g., Inductively Coupled Plasma Mass Spectrometer (ICP-MS)), and a resultant ion cloud (or multiple resultant ion clouds) produced by a single cell is analyzed (e.g., multiple times) by mass spectrometry (e.g., time of-flight mass spectrometry). Mass cytometry can use elements (e.g., a metal) or stable isotopes, attached as label moieties to a detection reagent (e.g., an antibody and/or a nucleic acid detection agent).

In other embodiments, detection may comprise sequence reads; probe binding and electrochemical detection; a change in pH; detection of catalysis induced by enzymes bound to DNA tags, detection by quantum entanglement, detection by Raman spectroscopy, detection by terahertz wave technology, detection by SEM (scanning electron microscopy).

Nucleic acids, analogs and mimetics. In defining the component oligonucleotide primers, probes, etc., used in the methods of the invention, it is to be understood that such probes, primers etc. encompass native and synthetic or modified polynucleotides, particularly the probes, primers etc. that are not themselves substrates for enzymatic modification during the performance of the method, e.g. the target specific oligonucleotide primers, and the detection probes.

A modified nucleic acid has one or more modifications, e.g., a base modification, a backbone modification, etc., to provide the nucleic acid with a new or enhanced feature (e.g., improved stability). A nucleoside can be a base-sugar combination, the base portion of which is a heterocyclic base. Heterocyclic bases include the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In some cases, the respective ends of this linear polymeric compound can be further joined to form a circular compound. In addition, linear compounds may have internal nucleotide base complementarity and may therefore fold in a manner as to produce a fully or partially double-stranded compound. Within oligonucleotides, the phosphate groups can be referred to as forming the internucleoside backbone of the oligonucleotide. The linkage or backbone of RNA and DNA can be a 3' to 5' phosphodiester linkage.

Examples of suitable nucleic acids containing modifications include nucleic acids with modified backbones or non-natural internucleoside linkages. Nucleic acids having modified backbones include those that retain a phosphorus atom in the backbone and those that do not have a phosphorus atom in the backbone. Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3',5' to 5' or 2' to 2' linkage. Suitable oligonucleotides having inverted polarity include a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid has one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in U.S. Pat. No. 5,602,240.

Also suitable are nucleic acids having morpholino backbone structures as described in, e.g., U.S. Pat. No. 5,034, 506. For example, in some embodiments, a subject nucleic acid includes a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Also included are nucleic acid mimetics. The term "mimetic" as it is applied to polynucleotides encompasses polynucleotides where only the furanose ring or both the furanose ring and the internucleotide linkage are replaced with non-furanose groups, replacement of only the furanose ring is also referred to as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of suitable polynucleotide mimetic is based on linked morpholino units (morpholino nucleic acid) having heterocyclic bases attached to the morpholino ring. A number of linking groups have been reported that can link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

Another suitable class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). The incorporation of CeNA monomers into a DNA chain increases the stability of a DNA/RNA hybrid. CeNA oligoadenylates formed complexes with RNA and DNA complements with similar stability to the native complexes. The incorporation CeNA structures into natural nucleic acid structures was shown by NMR and circular dichroism to proceed with conformational adaptation.

Also suitable as modified nucleic acids are Locked Nucleic Acids (LNAs) and/or LNA analogs. In an LNA, the 2'-hydroxyl group is linked to the 4' carbon atom of the sugar ring thereby forming a 2'-C,4'-C-oxymethylene linkage, and thereby forming a bicyclic sugar moiety. The linkage can be a methylene ($—CH_2—$), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO98/39352 and WO99/14226, both of which are hereby incorporated by reference in their entirety. Exemplary LNA analogs are described in U.S. Pat. Nos. 7,399,845 and 7,569,686, both of which are hereby incorporated by reference in their entirety.

A nucleic acid can also include one or more substituted sugar moieties. Suitable polynucleotides include a sugar substituent group selected from: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides include a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, and other substituents having similar properties. A suitable modification can include 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A suitable modification can include 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also referred to as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$)

and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

A nucleic acid may also include a nucleobase (also referred to as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Modified nucleobases also include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), and pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Quantitation of detectable label. Various methods can be utilized for quantifying the presence of a detectable label, either on the detection probe, or present in a combined method with analysis of cellular markers used to define the cell being analyzed. For measuring the amount of a detection probe, or other specific binding partner that is present, a convenient method is to label with a detectable moiety, which may be a metal, fluorescent, luminescent, radioactive, enzymatically active, etc.

Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81).

Mass cytometry is a variation of flow cytometry in which probes are labeled with heavy metal ion tags rather than fluorochromes. Readout is by time-of-flight mass spectrometry. This allows for the combination of many more specificities in a single samples, without significant spillover between channels. For example, see Bendall et al. (2011) Science 332 (6030): 687-696, herein specifically incorporated by reference. Scanning mass spectrometry (including, but not limited to nano-SIMS) is an alternative method of detecting metal labels.

Multiple fluorescent or metal labels can be used on the same sample and individually detected quantitatively, permitting simultaneous multiplex analysis. Many quantitative techniques have been developed to harness the unique properties of fluorescence including: direct fluorescence measurements, fluorescence resonance energy transfer (FRET), fluorescence polarization or anisotropy (FP), time resolved fluorescence (TRF), fluorescence lifetime measurements (FLM), fluorescence correlation spectroscopy (FCS), and fluorescence photobleaching recovery (FPR) (Handbook of Fluorescent Probes and Research Chemicals, Seventh Edition, Molecular Probes, Eugene Oreg.).

Flow or mass cytometry may be used to quantitate parameters such as the presence of cell surface proteins or conformational or posttranslational modification thereof; intracellular or secreted protein, where permeabilization allows antibody (or probe) access, and the like. Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998.

Cells. Cells for use in the assays of the invention can be an organism, a single cell type derived from an organism, or can be a mixture of cell types. Included are naturally occurring cells and cell populations, genetically engineered cell lines, cells derived from transgenic animals, etc. Virtually any cell type and size can be accommodated. Suitable cells include bacterial, fungal, plant and animal cells. In one embodiment of the invention, the cells are mammalian cells, e.g. complex cell populations such as naturally occurring tissues, for example blood, liver, pancreas, neural tissue, bone marrow, skin, and the like. Some tissues may be disrupted into a monodisperse suspension. Alternatively, the cells may be a cultured population, e.g. a culture derived from a complex population, a culture derived from a single cell type where the cells have differentiated into multiple lineages, or where the cells are responding differentially to stimulus, and the like.

Cell types that can find use in the subject invention include stem and progenitor cells, e.g. embryonic stem cells, hematopoietic stem cells, mesenchymal stem cells, neural crest cells, etc., endothelial cells, muscle cells, myocardial, smooth and skeletal muscle cells, mesenchymal cells, epithelial cells; hematopoietic cells, such as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells; etc.; adipocytes, cells involved with particular organs, such as thymus, endocrine glands, pancreas, brain, such as neurons, glia, astrocytes, dendrocytes, etc. and genetically modified cells thereof. Hematopoietic cells may be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc.

The cells may also be transformed or neoplastic cells of different types, e.g. carcinomas of different cell origins, lymphomas of different cell types, etc. The American Type Culture Collection (Manassas, VA) has collected and makes available over 4,000 cell lines from over 150 different species, over 950 cancer cell lines including 700 human cancer cell lines. The National Cancer Institute has compiled clinical, biochemical and molecular data from a large panel of human tumor cell lines, these are available from ATCC or the NCI (Phelps et al. (1996) *Journal of Cellular Biochemistry* Supplement 24:32-91). Included are different cell lines derived spontaneously, or selected for desired growth or response characteristics from an individual cell line; and may include multiple cell lines derived from a similar tumor type but from distinct patients or sites.

Cells may be non-adherent, e.g. blood cells including monocytes, T cells, B-cells; tumor cells, etc., or adherent cells, e.g. epithelial cells, endothelial cells, neural cells, etc. In order to profile adherent cells, they may be dissociated from the substrate that they are adhered to, and from other cells, in a manner that maintains their ability to recognize and bind to probe molecules.

Such cells can be acquired from an individual using, e.g., a draw, a lavage, a wash, surgical dissection etc., from a variety of tissues, e.g., blood, marrow, a solid tissue (e.g., a solid tumor), ascites, by a variety of techniques that are known in the art. Cells may be obtained from fixed or unfixed, fresh or frozen, whole or disaggregated samples. Disaggregation of tissue may occur either mechanically or enzymatically using known techniques.

Various methods and devices exist for pre-separating component parts of the sample. These methods include filters, centrifuges, chromatographs, and other well-known fluid separation methods; gross separation using columns, centrifuges, filters, separation by killing of unwanted cells, separation with fluorescence activated cell sorters, separation by directly or indirectly binding cells to a ligand immobilized on a physical support, such as panning techniques, separation by column immunoadsorption, and separation using magnetic immunobeads.

Fixation and permeabilization. Aspects of the invention include "fixing" a cellular sample. The term "fixing" or "fixation" as used herein is the process of preserving biological material (e.g., tissues, cells, organelles, molecules, etc.) from decay and/or degradation. Fixation may be accomplished using any convenient protocol. Fixation can include contacting the cellular sample with a fixation reagent (i.e., a reagent that contains at least one fixative). Cellular samples can be contacted by a fixation reagent for a wide range of times, which can depend on the temperature, the nature of the sample, and on the fixative(s). For example, a cellular sample can be contacted by a fixation reagent for 24 or less hours, 18 or less hours, 12 or less hours, 8 or less hours, 6 or less hours, 4 or less hours, 2 or less hours, 60 or less minutes, 45 or less minutes, 30 or less minutes, 25 or less minutes, 20 or less minutes, 15 or less minutes, 10 or less minutes, 5 or less minutes, or 2 or less minutes.

A cellular sample can be contacted by a fixation reagent for a period of time in a range of from 5 minutes to 24 hours (e.g., from 10 minutes to 20 hours, from 10 minutes to 18 hours, from 10 minutes to 12 hours, from 10 minutes to 8 hours, from 10 minutes to 6 hours, from 10 minutes to 4 hours, from 10 minutes to 2 hours, from 15 minutes to 20 hours, from 15 minutes to 18 hours, from 15 minutes to 12 hours, from 15 minutes to 8 hours, from 15 minutes to 6 hours, from 15 minutes to 4 hours, from 15 minutes to 2 hours, from 15 minutes to 1.5 hours, from 15 minutes to 1 hour, from 10 minutes to 30 minutes, from 15 minutes to 30 minutes, from 30 minutes to 2 hours, from 45 minutes to 1.5 hours, or from 55 minutes to 70 minutes).

A cellular sample can be contacted by a fixation reagent at various temperatures, depending on the protocol and the reagent used. For example, in some instances a cellular sample can be contacted by a fixation reagent at a temperature ranging from −22° C. to 55° C., where specific ranges of interest include, but are not limited to: 50 to 54° C., 40 to 44° C., 35 to 39° C., 28 to 32° C., 20 to 26° C., 0 to 6° C., and −18 to −22° C. In some instances a cellular sample can be contacted by a fixation reagent at a temperature of −20° C., 4° C., room temperature (22-25° C.), 30° C., 37° C., 42° C., or 52° C.

Any convenient fixation reagent can be used. Common fixation reagents include crosslinking fixatives, precipitating fixatives, oxidizing fixatives, mercurials, and the like. Cross-linking fixatives chemically join two or more molecules by a covalent bond and a wide range of cross-linking reagents can be used. Examples of suitable cross-liking fixatives include but are not limited to aldehydes (e.g., formaldehyde, also commonly referred to as "paraformaldehyde" and "formalin"; glutaraldehyde; etc.), imidoesters, NHS (N-Hydroxysuccinimide) esters, and the like. Examples of suitable precipitating fixatives include but are not limited to alcohols (e.g., methanol, ethanol, etc.), acetone, acetic acid, etc. In some embodiments, the fixative is formaldehyde (i.e., paraformaldehyde or formalin). A suitable final concentration of formaldehyde in a fixation reagent is 0.1 to 10%, 1-8%, 1-4%, 1-2%, 3-5%, or 3.5-4.5%, including about 1.6% for 10 minutes. In some embodiments the cellular sample is fixed in a final concentration of 4% formaldehyde (as diluted from a more concentrated stock solution, e.g., 38%, 37%, 36%, 20%, 18%, 16%, 14%, 10%, 8%, 6%, etc.). In some embodiments the cellular sample is fixed in a final concentration of 10% formaldehyde. In some embodiments the cellular sample is fixed in a final concentration of 1% formaldehyde. In some embodiments, the fixative is glutaraldehyde. A suitable concentration of glutaraldehyde in a fixation reagent is 0.1 to 1%.

A fixation reagent can contain more than one fixative in any combination. For example, in some embodiments the cellular sample is contacted with a fixation reagent containing both formaldehyde and glutaraldehyde.

Permeabilization. Aspects of the invention include "permeabilizing" a cellular sample. The terms "permeabilization" or "permeabilize" as used herein refer to the process of rendering the cells (cell membranes etc.) of a cellular sample permeable to experimental reagents such as nucleic acid probes, antibodies, chemical substrates, etc. Any convenient method and/or reagent for permeabilization can be used. Suitable permeabilization reagents include detergents (e.g., Saponin, Triton X-100, Tween-20, etc.), organic fixatives (e.g., acetone, methanol, ethanol, etc.), enzymes, etc. Detergents can be used at a range of concentrations. For example, 0.001%-1% detergent, 0.05%-0.5% detergent, or 0.1%-0.3% detergent can be used for permeabilization (e.g., 0.1% Saponin, 0.2% tween-20, 0.1-0.3% triton X-100, etc.). In some embodiments methanol on ice for at least 10 minutes is used to permeabilize.

In some embodiments, the same solution can be used as the fixation reagent and the permeabilization reagent. For example, in some embodiments, the fixation reagent contains 0.1%-10% formaldehyde and 0.001%-1% saponin. In some embodiments, the fixation reagent contains 1% formaldehyde and 0.3% saponin.

A cellular sample can be contacted by a permeabilization reagent for a wide range of times, which can depend on the temperature, the nature of the sample, and on the permeabilization reagent(s). For example, a cellular sample can be contacted by a permeabilization reagent for 24 or more hours (see storage described below), 24 or less hours, 18 or less hours, 12 or less hours, 8 or less hours, 6 or less hours, 4 or less hours, 2 or less hours, 60 or less minutes, 45 or less minutes, 30 or less minutes, 25 or less minutes, 20 or less minutes, 15 or less minutes, 10 or less minutes, 5 or less minutes, or 2 or less minutes. A cellular sample can be contacted by a permeabilization reagent at various temperatures, depending on the protocol and the reagent used. For example, in some instances a cellular sample can be contacted by a permeabilization reagent at a temperature ranging from −82° C. to 55° C., where specific ranges of interest include, but are not limited to: 50 to 54° C., 40 to 44° C., 35 to 39° C., 28 to 32° C., 20 to 26° C., 0 to 6° C., −18 to −22° C., and −78 to −82° C. In some instances a cellular sample can be contacted by a permeabilization reagent at a temperature of −80° C., −20° C., 4° C., room temperature (22-25° C.), 30° C., 37° C., 42° C., or 52° C.

In some embodiments, a cellular sample is contacted with an enzymatic permeabilization reagent. Enzymatic permeabilization reagents that permeabilize a cellular sample by partially degrading extracellular matrix or surface proteins that hinder the permeation of the cellular sample by assay reagents. Contact with an enzymatic permeabilization reagent can take place at any point after fixation and prior to target detection. In some instances the enzymatic permeabilization reagent is proteinase K, a commercially available enzyme. In such cases, the cellular sample is contacted with proteinase K prior to contact with a post-fixation reagent (described below). Proteinase K treatment (i.e., contact by proteinase K; also commonly referred to as "proteinase K digestion") can be performed over a range of times at a range of temperatures, over a range of enzyme concentrations that are empirically determined for each cell type or tissue type under investigation. For examples, a cellular sample can be contacted by proteinase K for 30 or less minutes, 25 or less minutes, 20 or less minutes, 15 or less minutes, 10 or less minutes, 5 or less minutes, or 2 or less minutes. A cellular sample can be contacted by 1 ug/ml or less, 2 ug/m or less I, 4 ug/ml or less, 8 ug/ml or less, 10 ug/ml or less, 20 ug/ml or less, 30 ug/ml or less, 50 ug/ml or less, or 100 ug/ml or less proteinase K. A cellular sample can be contacted by proteinase K at a temperature ranging from 2° C. to 55° C., where specific ranges of interest include, but are not limited to: 50 to 54° C., 40 to 44° C., 35 to 39° C., 28 to 32° C., 20 to 26° C., and 0 to 6° C. In some instances a cellular sample can be contacted by proteinase K at a temperature of 4° C., room temperature (22-25° C.), 30° C., 37° C., 42° C., or 52° C. In some embodiments, a cellular sample is not contacted with an enzymatic permeabilization reagent. In some embodiments, a cellular sample is not contacted with proteinase K.

Contact of a cellular sample with at least a fixation reagent and a permeabilization reagent results in the production of a fixed/permeabilized cellular sample.

Nuclease inhibition. Aspects of the invention include contacting a cellular sample with a nuclease inhibitor during hybridization steps, particularly during binding of the target specific oligonucleotide pair to RNA molecules present in the cell. As used herein, a "nuclease inhibitor" is any molecule that can be used to inhibit nuclease activity within the cellular sample such that integrity of the nucleic acids within the cells of the cellular sample is preserved. In other words, degradation of the nucleic acids within the cells of the cellular sample by nuclease activity is inhibited by contacting the cellular sample with a nuclease inhibitor.

In some embodiments, the nuclease inhibitor is an RNase inhibitor (i.e., the inhibitor inhibits RNase activity). Examples of suitable commercially available nuclease inhibitors include, protein and non-protein based inhibitors, e.g. vanadyl ribonucleoside complexes, Oligo(vinylsulfonic Acid) (OVS), 2.5%, aurintricarboxylic acid (ATA); Diethyl Pyrocarbonate (DEPC); RNAsecure™ Reagent from Life Technologies; and the like) and protein based inhibitors (e.g., ribonuclease inhibitor from EMD Millipore; RNase-OUT™ Recombinant Ribonuclease Inhibitor, SUPERaseIn™, ANTI-RNase, and RNase Inhibitor from Life Technologies; RNase Inhibitor and Protector RNase Inhibitor from Roche; RNAsin from Promega, and the like). Nuclease inhibitors can be used at a range of concentrations as recommended by their commercial sources.

Marker detection reagents. Aspects of the invention may include contacting the cells in a sample with a detection reagent in order to profile cells simultaneously for markers in addition to the target nucleic acids. Such methods are particularly useful in detecting the phenotype of cells in complex populations, e.g. populations of immune cells, populations of neural cells, complex biopsy cell populations, and the like. The term "marker detection reagent" as used herein refers to any reagent that specifically binds to a target marker (e.g., a target protein of a cell of the cellular sample) and facilitates the qualitative and/or quantitative detection of the target protein. The terms "specific binding," "specifically binds," and the like, refer to the preferential binding to a molecule relative to other molecules or moieties in a solution or reaction mixture. In some embodiments, the affinity between detection reagent and the target protein to which it specifically binds when they are specifically bound to each other in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. "Affinity" refers to the strength of binding, increased binding affinity being correlated with a lower $K_d$.

In some embodiments, a protein detection reagent includes a label or a labeled binding member. A "label" or "label moiety" is any moiety that provides for signal detection and may vary widely depending on the particular nature of the assay, and includes any of the labels suitable for use with the oligonucleotide detection probe, described above.

In some instances, a protein detection reagent is a polyclonal or monoclonal antibody or a binding fragment thereof (i.e., an antibody fragment that is sufficient to bind to the target of interest, e.g., the protein target). Antibody fragments (i.e., binding fragments) can be, for example, monomeric Fab fragments, monomeric Fab' fragments, or dimeric F(ab)'$_2$ fragments. Also within the scope of the term "antibody or a binding fragment thereof" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

Markers of interest include cytoplasmic, cell surface or secreted biomolecules, frequently biopolymers, e.g. polypeptides, polysaccharides, polynucleotides, lipids, etc. Where the marker is a protein the detection may include states of phosphorylation, glycosylation, and the like as known in the art.

Methods of Use

Multiplexed assays as demonstrated here save time and effort, as well as precious clinical material, and permit analysis of genetic events such as copy number amplification, RNA expression etc. at a single cell level. More importantly, the ability to simultaneously assess multiple concurrent molecular events within the same cells can provide entirely new opportunities to elucidate the intricate networks of interactions within cells. Multiplexed analysis can be used to measure and quantify the balance between genetic interactions for an improved understanding of cellular functions.

Aspects of the invention include methods of assaying a cellular sample for the presence of a target nucleic acid (e.g., deoxyribonucleic acid, ribonucleic acid) at the single cell level, usually a plurality of target nucleic acids at a single cell level. The analysis can be combined with analysis of additional markers that define cells within the population, e.g. protein markers.

As such, methods of the invention are methods of evaluating the amount (i.e., level) of a target nucleic acid in a cell of a cellular sample. In some embodiments, methods of the invention are methods of evaluating whether a target nucleic acid is present in a sample, where the detection of the target nucleic acid is qualitative. In some embodiments, methods of the invention are methods of evaluating whether a target nucleic acid is present in a sample, where the detection of the target nucleic acid is quantitative. The methods can include determining a quantitative measure of the amount of a target nucleic acid in a cell of a cellular sample. In some embodiments, quantifying the level of expression of a target nucleic acid includes comparing the level of expression of one nucleic acid to the level of expression of another nucleic acid in order to determine a relative level of expression. In some embodiments, the methods include determining whether a target nucleic acid is present above or below a predetermined threshold in a cell of a cellular sample. As such, when the detected signal is greater than a particular threshold (also referred to as a "predetermined threshold"), the amount of target nucleic acid of interest is present above the predetermined threshold in the cell of a cellular sample. When the detected signal is weaker than a predetermined threshold, the amount of target nucleic acid of interest is present below the predetermined threshold in the cell of a cellular sample.

The term "cellular sample," as used herein means any sample containing one or more individual cells in suspension at any desired concentration. For example, the cellular sample can contain $10^{11}$ or less, $10^{10}$ or less, 109 or less, $10^8$ or less, 107 or less, $10^6$ or less, 105 or less, 104 or less, 103 or less, 500 or less, 100 or less, 10 or less, or one cell per milliliter. The sample can contain a known number of cells or an unknown number of cells. Suitable cells include eukaryotic cells (e.g., mammalian cells) and/or prokaryotic cells (e.g., bacterial cells or archaeal cells).

In practicing the methods of the invention, the cellular sample can be obtained from an in vitro source (e.g., a suspension of cells from laboratory cells grown in culture) or from an in vivo source (e.g., a mammalian subject, a human subject, etc.). In some embodiments, the cellular sample is obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, the sample is obtained from an in vivo source and can include samples obtained from tissues (e.g., cell suspension from a tissue biopsy, cell suspension from a tissue sample, etc.) and/or body fluids (e.g., whole blood, fractionated blood, plasma, serum, saliva, lymphatic fluid, interstitial fluid, etc.). In some cases, cells, fluids, or tissues derived from a subject are cultured, stored, or manipulated prior to evaluation. In vivo sources include living multi-cellular organisms and can yield non-diagnostic or diagnostic cellular samples.

Cellular samples can be obtained from a variety of different types of subjects. In some embodiments, a sample is from a subject within the class mammalia, including e.g., the orders carnivore (e.g., dogs and cats), rodentia (e.g., mice, guinea pigs, and rats), lagomorpha (e.g. rabbits) and primates (e.g., humans, chimpanzees, and monkeys), and the like. In certain embodiments, the animals or hosts, i.e., subjects (also referred to herein as patients) are humans.

Aspects of the invention may include contacting the cellular sample with a "stimulating agent", also referred to herein as a "stimulator." By stimulating agent it is meant any compound that affects at least one cellular activity or that alters the cellular steady state (i.e., induced or reduced in abundance or activity). Contacting a cellular sample with a stimulating agent can be used to ascertain the cellular response to the agent. By "effective amount" of a stimulating agent, it is meant that a stimulating agent is present in an amount to affect at least one cellular activity that alters the cellular steady state (i.e., induced or reduced in abundance or activity). A stimulating agent can be provided as a powder or as a liquid. As such, a stimulating agent can include various compounds and formulations, such as intracellular signal inducing and immunomodulatory agents. Examples include small molecule drugs as well as peptides, proteins, lipids carbohydrates and the like. Of particular interest are compounds such as peptide hormones, chemokines, cytokines, e.g. type I interferons (e.g., IFN-α, IFN-β), interleukins (e.g., interleukin-2 (IL-2), IL-4, IL-6, IL-7, IL-10, IL-12, IL-15, IL-21), tumor necrosis factor alpha (TNF-α), gamma interferon (IFN-γ), transforming growth factor β, and the like.

Target Nucleic Acid Detection

The subject methods are methods of assaying for the presence of a target nucleic acid. As such, the subject methods are methods (when a target nucleic acid is present in a cell of a cellular sample) of detecting the target nucleic acid, producing a signal in response to target nucleic acid detection, and detecting the produced signal. The signal produced by a detected target nucleic acid can be any detectable signal (e.g., a fluorescent signal, an amplified fluorescent signal, a chemiluminescent signal, etc.)

Aspects of the invention include methods of detecting a target nucleic acid (i.e., target nucleic acid detection). In some embodiments, the cellular sample is contacted with a nucleic acid detection agent. As used herein, the term "nucleic acid detection agent" means any reagent that can specifically bind to a target nucleic acid. For example, suitable nucleic acid detection agents can be nucleic acids (or modified nucleic acids) that are at least partially complementary to and hybridize with a sequence of the target nucleic acid. In some embodiments, the nucleic acid detection agent includes a probe or set of probes (i.e., probe set), each of which specifically binds (i.e., hybridizes to) a sequence (i.e., target sequence) of the target nucleic acid.

In some embodiments, a method is provided for determining the abundance of a target nucleic acid in a single cell, the method comprising contacting a fixed and permeabilized cell with a pair of oligonucleotide SNAIL primers under conditions permissive for specific hybridization; washing the cells free of unbound primers; performing a ligation reaction, in which a SNAIL oligonucleotide is ligated to generate a circle; amplifying the ligated circle by rolling circle amplification; hybridizing detection primers to the amplified circle; and quantitating the level of bound detection primers to determine the abundance of the target nucleic acid.

In some embodiments of the invention, SNAIL is used in combination with cytometry gating on specific cell populations, as defined by other cellular parameters measured simultaneously, for example in combination with antibody staining and mass cytometry or FACS to define a subpopulation of interest. In such embodiments, a complex cell population may be analyzed, e.g. a biopsy or blood sample potentially including immune cells, progenitor or stem cells, cancer cells, etc. For example, a method is provided for determining the abundance of one or more target nucleic acids in a defined cell type within a complex cell population, where the quantification of detection probes is combined with detection of cellular markers, including without limitation protein markers, that serve to define the cell type of interest.

In other embodiments, the methods of the invention are used for multiplexed detection and quantification of specific splice variants of mRNA transcripts in single cells.

In yet another embodiment, the methods of the invention are combined with Proximity Ligation Assay (PLA) for the simultaneous detection and quantification of nucleic acid molecules and protein-protein interactions.

With prior denaturation of endogenous cellular DNA (by heat, enzymatic methods, or any other suitable procedure), the technology is modified for the detection of specific DNA sequences (genotyping of single cells). In this adaptation, the technology enables the quantification of gene copy number variations as well as the detection of genomic translocation/fusion events.

Signal detection and quantitation can be carried out using any instrument (e.g., liquid assay device) that can measure the fluorescent, luminescent, light-scattering or colorimetric signal(s) output from the subject methods. In some embodiments, the signal resulting from the detection of a target nucleic acid is detected by a flow cytometer. In some embodiments, a liquid assay device for evaluating a cellular sample for the presence of the target nucleic acid is a flow cytometer, e.g. mass cytometer, FACS, MACS, etc. As such, in some instances, the evaluation of whether a target nucleic acid is present in a cell of a cellular sample includes flow cytometrically analyzing the cellular sample. In flow cytometry, cells of a cellular sample are suspended in a stream of fluid, which is passed, one cell at a time, by at least one beam of light (e.g., a laser light of a single wavelength). A number of detectors, including one or more fluorescence detectors, detect scattered light as well as light emitted from the cellular sample (e.g., fluorescence). In this way, the flow cytometer acquires data that can be used to derive information about the physical and chemical structure of each individual cell that passes through the beam(s) of light. If a signal specific to the detection of a target nucleic acid is detected in a cell by the flow cytometer, then the target nucleic acid is present in the cell. In some embodiments, the detected signal is quantified using the flow cytometer.

The readout may be a mean, average, median or the variance or other statistically or mathematically-derived value associated with the measurement. The readout information may be further refined by direct comparison with the corresponding reference or control, e.g. by reference to a standard polynucleotide sample, housekeeping gene expression, etc. The absolute values obtained for under identical conditions may display a variability that is inherent in live biological systems.

In certain embodiments, the obtained data is compared to a single reference/control profile to obtain information regarding the phenotype of the cell being assayed. In yet other embodiments, the obtained data is compared to two or more different reference/control profiles to obtain more in depth information regarding the phenotype of the cell. For example, the obtained data may be compared to a positive and negative controls to obtain confirmed information regarding whether a cell has a phenotype of interest.

Utility

The methods, devices, compositions and kits of the invention find use in a variety of different applications. Methods of the invention are methods of evaluating cells of a cellular sample, where the target nucleic acid may or may not be present. In some cases, it is unknown prior to performing the assay whether a cell of the cellular sample expresses the target nucleic acid. In other instances, it is unknown prior to performing the assay whether a cell of the cellular sample expresses the target nucleic acid in an amount (or relative amount, e.g., relative to another nucleic acid or relative to the amount of the target nucleic acid in a normal cell) that is greater than (exceeds) a predetermined threshold amount (or relative amount). In such cases, the methods are methods of evaluating cells of a cellular sample in which the target nucleic acid of interest may or may not be present in an amount that is greater than (exceeds) or below than a predetermined threshold. In some embodiments, the methods of the invention can be used to determine the expression level (or relative expression level) of a nucleic acid in individual cell(s) of a cellular sample, usually a multiplex analysis of multiple nucleic acids in a cell. Optionally additional markers such as proteins are also analyzed.

The methods of the invention can be used to identify specific cells in a sample as aberrant or non-aberrant. For example, some mRNAs are known to be expressed above a particular level, or relative level, (i.e., above a predetermined threshold) in aberrant cells (e.g., cancerous cells). Thus, when the level (or relative level) of signal (as detected using the subject methods) for a particular target nucleic acid (e.g., mRNA) of a cell of the cellular sample indicates that the level (or relative level) of the target nucleic acid is equal to or greater than the level (or relative level) known to be associated with an aberrant cell, then the cell of the cellular sample is determined to be aberrant. To the contrary, some mRNAs (and/or miRNAs) are known to be expressed below a particular level, or relative level, (i.e., below a predetermined threshold) in aberrant cells (e.g., cancerous cells). Thus, when the level (or relative level) of signal (as detected using the subject methods) for a particular target nucleic acid of a cell of the cellular sample indicates that the level (or relative level) of the target nucleic acid is equal to or less than the level (or relative level) known to be associated with an aberrant cell, then the cell of the cellular sample is determined to be aberrant. Therefore, the subject methods can be used to detect and count the number and/or frequency of aberrant cells in a cellular sample. Any identified cell of interest can be profiled for additional information with respect to protein or other markers.

In some instances, it is unknown whether the expression of a particular target nucleic acid varies in aberrant cells and the methods of the invention can be used to determine whether expression of the target nucleic varies in aberrant cells. For example, a cellular sample known to contain no aberrant cells can be evaluated and the results can be compared to an evaluation of a cellular sample known (or suspected) to contain aberrant cells.

In some instances, an aberrant cell is a cell in an aberrant state (e.g., aberrant metabolic state; state of stimulation; state of signaling; state of disease; e.g., cell proliferative disease, cancer; etc.). In some instances, an aberrant cell is a cell that contains a prokaryotic, eukaryotic, or viral pathogen. In some cases, an aberrant pathogen-containing cell (i.e., an infected cell) expresses a pathogenic mRNA or a host cell mRNA at a level above cells that are not infected. In some cases, such a cell expresses a host cell mRNA at a level below cells that are not infected.

In embodiments that employ a flow cytometer to flow cytometrically analyze the cellular sample, evaluation of cells of the cellular sample for the presence of a target nucleic acid can be accomplished quickly, cells can be sorted, and large numbers of cells can be evaluated. Gating can be used to evaluate a selected subset of cells of the cellular sample (e.g., cells within a particular range of morphologies, e.g., forward and side-scattering characteristics; cells that express a particular combination of surface proteins; cells that express particular surface proteins at particular levels; etc.) for the presence or the level (or relative level) of expression of a target nucleic acid.

In some embodiments, the methods are methods of determining whether an aberrant cell is present in a diagnostic cellular sample. In other words, the sample has been obtained from or derived from an in vivo source (i.e., a living multi-cellular organism, e.g., mammal) to determine the presence of a target nucleic acid in one or more aberrant cells in order to make a diagnosis (i.e., diagnose a disease or condition). Accordingly, the methods are diagnostic methods. As the methods are "diagnostic methods," they are methods that diagnose (i.e., determine the presence or absence of) a disease (e.g., cancer, circulating tumor cell(s), minimal residual disease (MRD), a cellular proliferative disease state, viral infection, e.g., HIV, etc.) or condition (e.g., presence of a pathogen) in a living organism, such as a mammal (e.g., a human). As such, certain embodiments of the present disclosure are methods that are employed to determine whether a living subject has a given disease or condition (e.g., cancer, circulating tumor cell(s), minimal residual disease (MRD), a cellular proliferative disease state, a viral infection, presence of a pathogen, etc.). "Diagnostic methods" also include methods that determine the severity or state of a given disease or condition based on the level (or relative level) of expression of at least one target nucleic acid.

In some embodiments, the methods are methods of determining whether an aberrant cell is present in a non-diagnostic cellular sample. A non-diagnostic cellular sample is a cellular sample that has been obtained from or derived from any in vitro or in vivo source, including a living multi-cellular organism (e.g., mammal), but not in order to make a diagnosis. In other words, the sample has been obtained to determine the presence of a target nucleic acid, but not in order to diagnose a disease or condition. Accordingly, such methods are non-diagnostic methods.

The results of such analysis may be compared to results obtained from reference compounds, concentration curves, controls, etc. The comparison of results is accomplished by the use of suitable deduction protocols, artificial evidence systems, statistical comparisons, etc. In particular embodiments, the method described above may be employed in a multiplex assay in which a heterogeneous population of cells is labeled with a plurality of distinguishably labeled binding agents.

A database of analytic information can be compiled. These databases may include results from known cell types, references from the analysis of cells treated under particular conditions, and the like. A data matrix may be generated, where each point of the data matrix corresponds to a readout from a cell, where data for each cell may comprise readouts from multiple labels. The readout may be a mean, median or the variance or other statistically or mathematically derived value associated with the measurement. The output readout information may be further refined by direct comparison with the corresponding reference readout. The absolute values obtained for each output under identical conditions will display a variability that is inherent in live biological systems and also reflects individual cellular variability as well as the variability inherent between individuals.

Kits

Also provided by the present disclosure are kits for practicing the method as described above. The subject kit contains reagents for performing the method described above and in certain embodiments may contain a plurality of probes and primers, including for example at least one pair of target specific oligonucleotide primers; a corresponding insert and backbone for a padlock probe; and a detection probe optionally labeled with a detectable moiety. The kit may also contain a reference sample to which results obtained from a test sample may be compared.

In addition to above-mentioned components, the subject kit may further include instructions for using the components of the kit to practice the methods described herein. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. In addition to above-mentioned components, the subject kit may include software to perform comparison of data.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

The invention will now be more fully described in association with some examples which are not to be construed as limiting for the invention.

Example 1

Multiplexed Single Molecule RNA Visualization with a Simplified Two-Probe Proximity Ligation System Quantifying the gene transcriptional activity on a single-cell level is key to studying cell phenotypic heterogeneity, differentiation processes and gene regulatory networks. Most modern single-cell expression profiling methods require cDNA production which limits the efficiency and introduces sequence bias. An alternative method of smRNA-FISH is limited to long transcripts. We created a simple two-probe proximity ligation system termed SNAIL-RCA that enables in situ amplification, detection and visualization of genes. RCA products are detected via hybridization of unlabeled detection probes coupled with single-nucleotide extension with fluorescent nucleotide analogs. Fluorescent imaging and automatic image analysis enable precise quantification of expression levels. Multiplexing is enabled through re-hybridization, which, combined with parse barcoding strategy enables simultaneous detection of hundreds or thousands of genes. We show that SNAIL enables detection of single-cell transcription heterogeneity in cell cultures as well as tissue samples, is sensitive enough to detect low-expressed transcripts.

System design, high signal specificity on HLADR NALM vs Jurkat. We designed a simplified proximity ligation technique for multiplex detection of nucleic acids, primarily RNA. The method is called SNAIL-RCA, which stands for Splint Nucleotide Assisted Intramolecular Ligation followed by Rolling Circle Amplification. As shown on FIG. 1A, the RNA serves as a scaffold for assembly of a complex that consists of two synthetic oligonucleotides. The two oligonucleotides contain stretches that are complementary to directly adjunct regions on the target mRNA. The upstream 'splint' oligonucleotide includes a 3'end sequence that is designed to serve scaffold for circularization of the downstream 'padlock' oligonucleotide. At the same time, the 'padlock' nucleotide includes a gene-specific detection sequence. The 5' and the 3' ends of the 'padlock' nucleotide are designed to anneal to the splint in a butt head-to-end fashion, enabling the ligation of the circularized form by the T4 DNA ligase (FIG. 1A).

Following circularization a strand-displacing φ29 polymerase is added which triggers the rolling circle amplification (RCA) of the 'padlock' and the gene-specific detection sequence that it contains. (FIG. 1B) The complimentary region between the 'splint' and the 'padlock' is designed to be short and a have a low melting temperature such that the complex formation, ligation and subsequent RCA can only happen in the presence of a specific scaffold RNA. This sequence of events determines the specificity of target RNA detection. Detection is achieved via hybridization of a specific primer (FIG. 1C) and single-base extension with fluorescent dNTP (FIG. 1D). FIG. 1E-F demonstrates highly specific detection of HLADRA mRNA detection in a NALM cells (FIG. 1E), at the same time Jurkat cells that are derived from T-cell lineage and are negative for HLADR demonstrate a complete absence of signal, confirming the specificity of SNAIL-RCA system.

SNAIL features a simplified design with two oligonucleotides, formed in a single hybridization step. A main advantage is simplification of oligo design procedure: while the RNA-complimentary sequence and the detection sequence are modified depending on the target, the ligation sequence always remains constant, so probe sets against large pools of genes can be designed in a completely automated fashion.

Tissue preparation and sectioning. Tissues were harvested from mice, snap-frozen in O.C.T. compound (Tissue-Tek) and stored at −80 C. When needed, tissues were sliced in 5 m sections onto poly-lysine-coated coverslips and stored at −80 for up to one month.

SNAIL protocol. Slices were allowed to dry and equilibrate at RT for 1' and immediately fixed with 4% PFA in PBS for 10' at room temperature. Tissues were then permeabilized in ice-cold methanol and incubated for 10' at −80 C. Methanol was then removed and tissues were rehydrated in PBS, 0.1% Tween (Sigma-Aldrich), and 40 U/mL RNasin (PBST-R) for 1' at RT. Hybridizations with SNAIL probes were performed in a buffer based on DEPC-treated water (Life Technologies) containing 1×SSC (Affymetrix), 2.5% v/v polyvinylsulfonic acid, 20 mM ribonucleoside vanadyl complex (New England Biolabs), 40 U/mL RNasin, 1% Tween, and 100 µg/mL salmon sperm DNA (Life Technologies). SNAIL probes were resuspended in DEPC-treated water at a concentration of 100 µM. Probes were heated to 90° C. for 5 min and then chilled on ice and added to the tissues in hybridization buffer at a final concentration of 100 nM. Tissues were incubated overnight at 40° C. under gentle agitation, and subsequently washed three times with PBST-R. Tissues were then incubated for 20 min in a buffer containing PBS, 4×SSC, 40 U/mL RNasin at 40° C. under soft agitation. After two washes with PBST-R, tissues were incubated for 2 hours with T4 DNA ligase (Thermo) at 37 C, followed by a 2 hours phi29 DNA polymerase (Thermo) at 30° C. Both enzymes were used according to manufacturers' instructions, with the addition of 40 U/mL RNasin. Tissues were then incubated with detection oligonucleotides at a concentration of 10 nM for 30 minutes at 37° C. in PBS, 1×SSC, 0.1% Tween, 40 U/mL RNasin.

Example 2

Multiplexed visualization of single RNA molecules in cells and tissues typically relies on smRNA-FISH, which uses multiple fluorescently labelled probes that are directly hybridized to mRNAs. However, prior approaches typically uses 48 20-nt probes that need to be hybridized to each mRNA, which could limit the approach to large mRNAs. Also, creating large libraries representing a large fraction of the genome might be prohibitively expensive. bDNA technology can detect short RNAs and even miRNAs, but its multiplexing is limited by the difficulty of finding orthogonal bDNA sequences. Alternatively, cDNA can be produced in situ and then hybridized with padlock probes, which are ligated and amplified via RCA, but low efficiency and sequence bias of reverse transcription pose a bottleneck to this approach.

Figure 2:
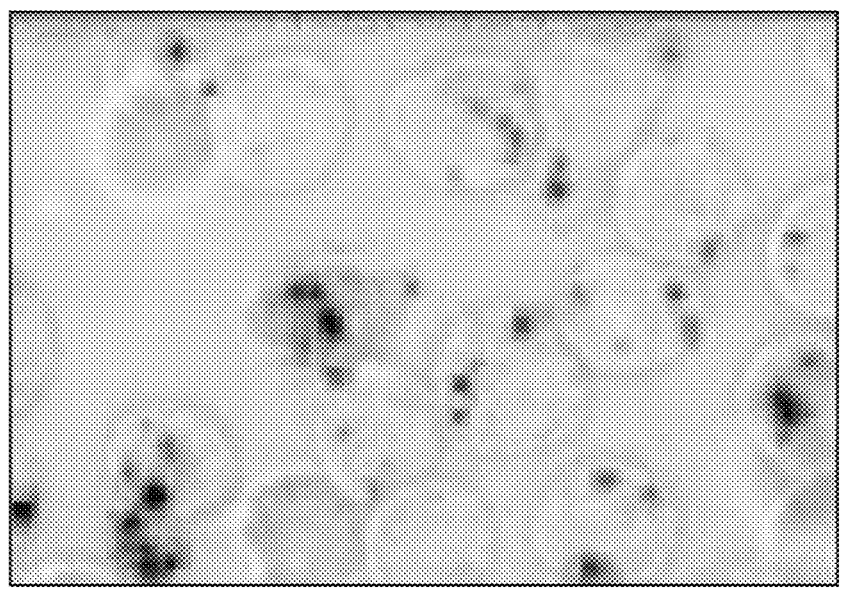
FIG. 2. SNAIL-RCA detection of expression of HLADR in NALM-6 and Jurkat cells.
Figure 2:
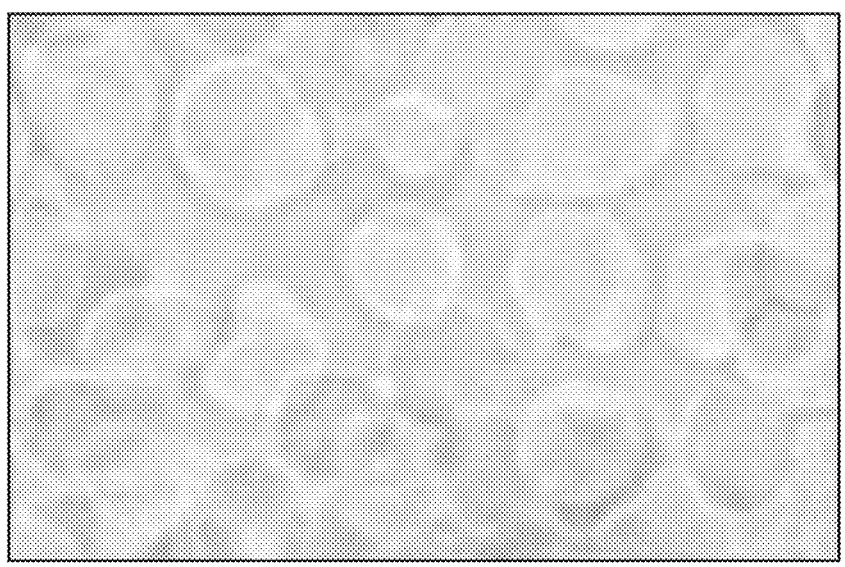

We conceived of a simplified design termed SNAIL-RCA (Specific Amplification of Nucleic Acids via Intramolecular Ligation and Rolling Circle Amplification) that uses two probes and eliminates a need for having adapter sequences—and which reduces the ligation reactions from 2 to 1 or none. The upstream probe serves as a splint for circularization and ligation of a downstream 'padlock' probe, which contains the detection barcode sequence (FIG. 1a). Each probe pair forms a circular construct upon hybridization to the target RNA, which is then ligated and amplified by a strand-displacing polymerase. (FIG. 1b) The melting temperature of the complementarity region is sufficiently low (Tm 27° C.). to prevent the formation of the two-probe dimer in the absence of the target mRNA during the hybridization (40° C.) and ligation (37° C.) steps. This amounts to high specificity of target detection, with virtually zero background, as evidenced by detection of HLADR and CD3 in B-cell leukemia (NALM-6) and T-cell leukemia (Jurkat) cell lines (FIG. 2).

Figure 3:
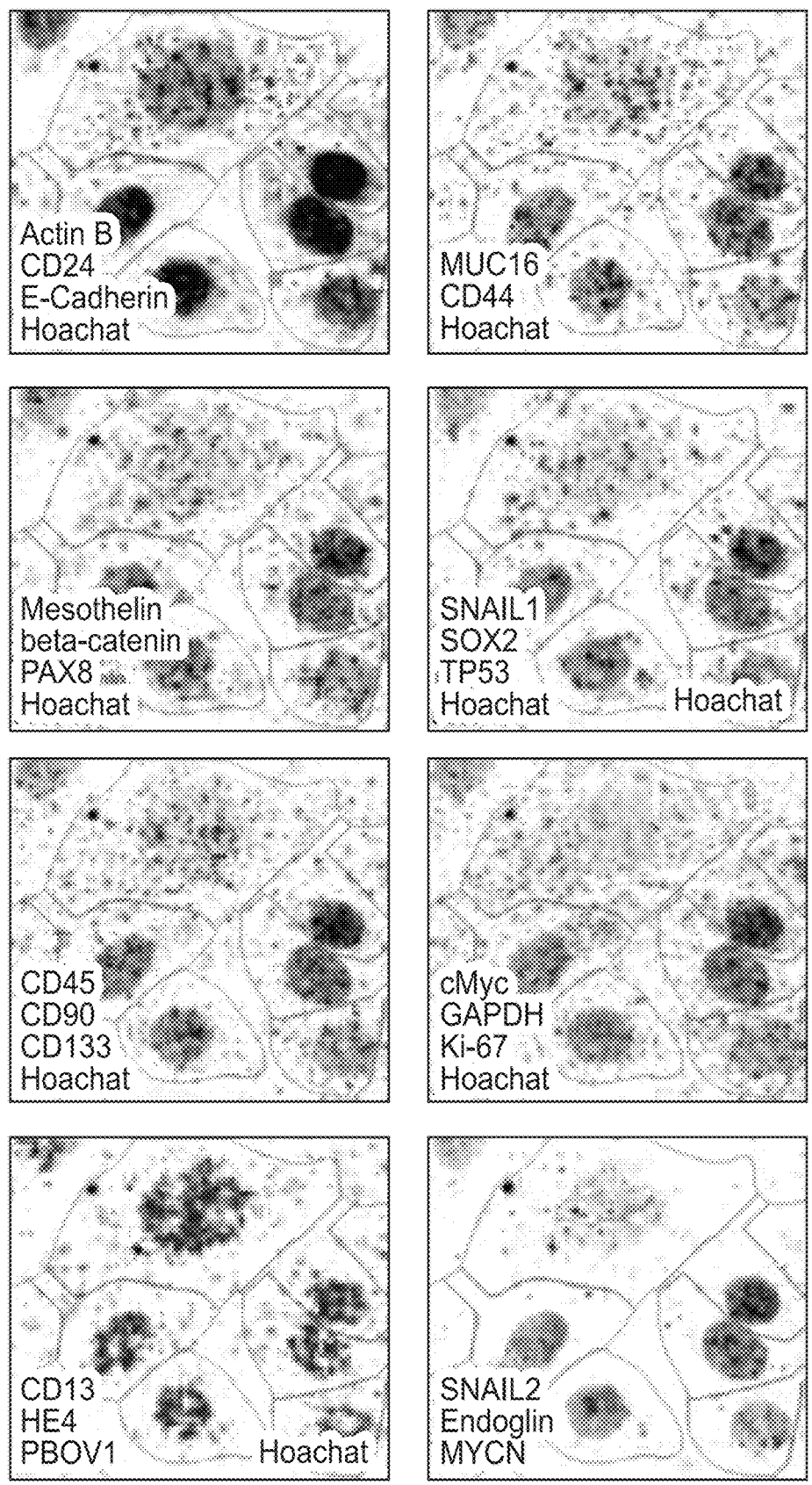
FIG. 3. Profiling of expression of 24 genes in OVCAR-4 cells, visualized by iterative reannealing of detection probes.
Figure 4A:
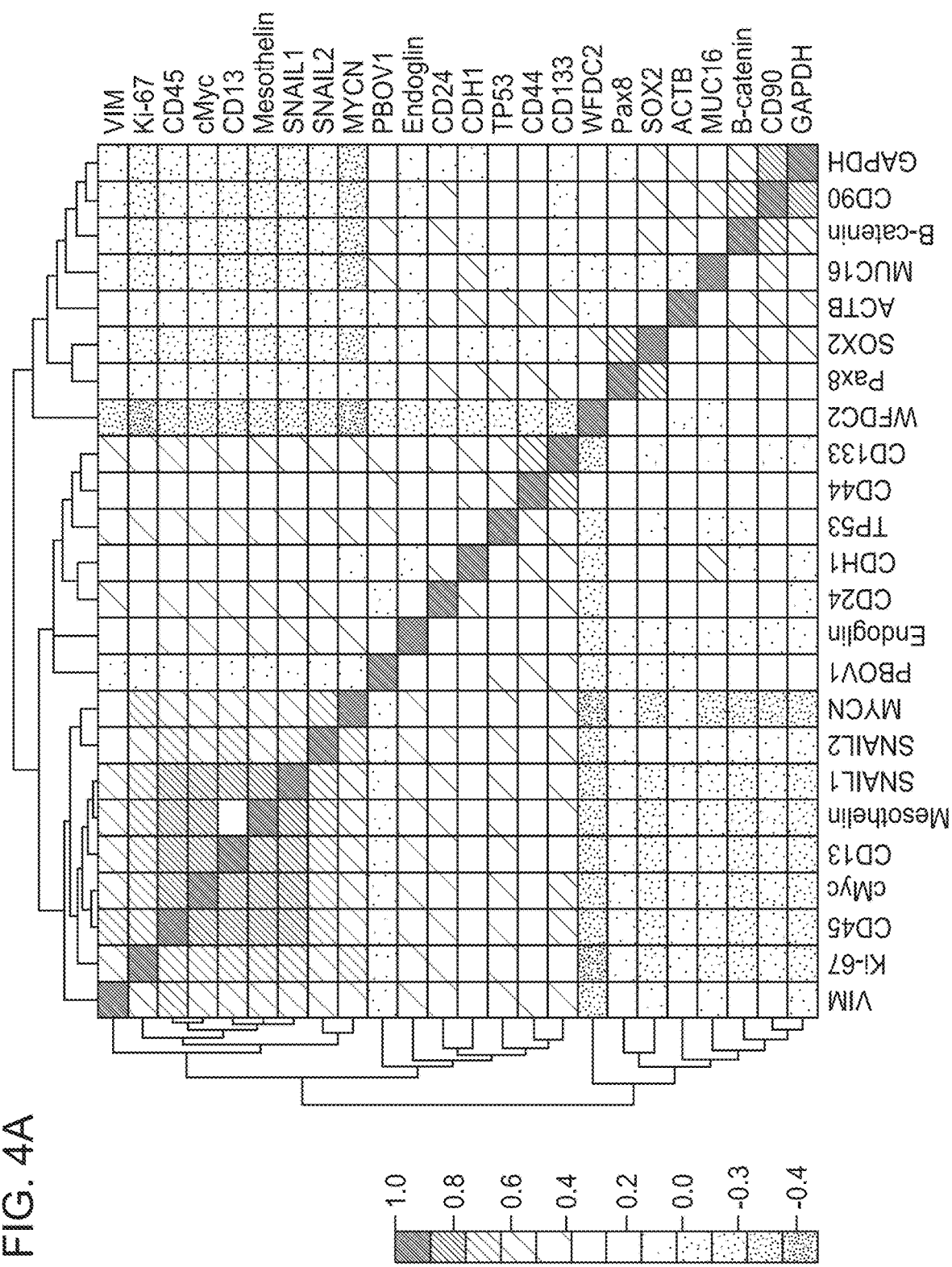
Figure 4B:
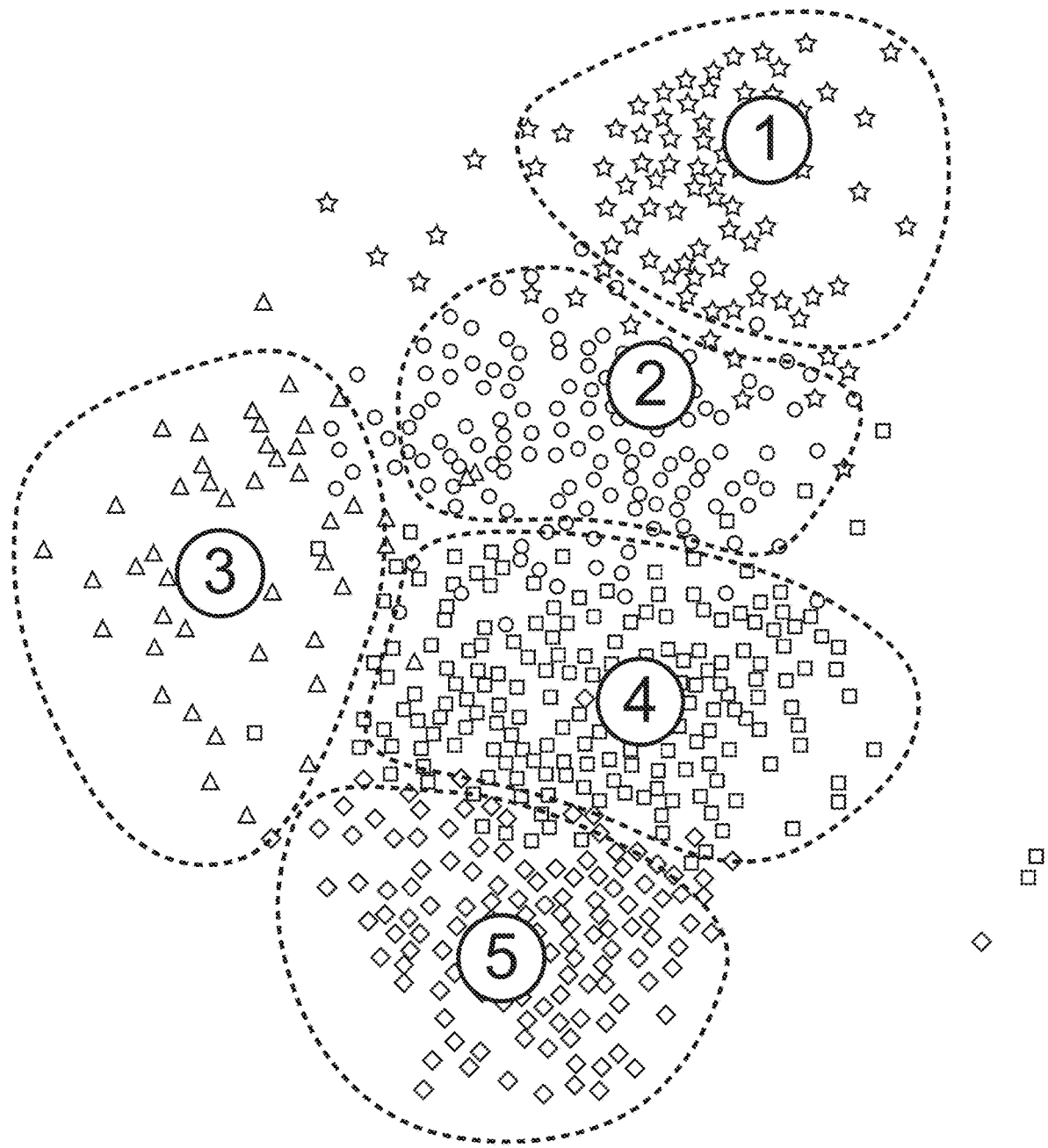
Figure 4C:
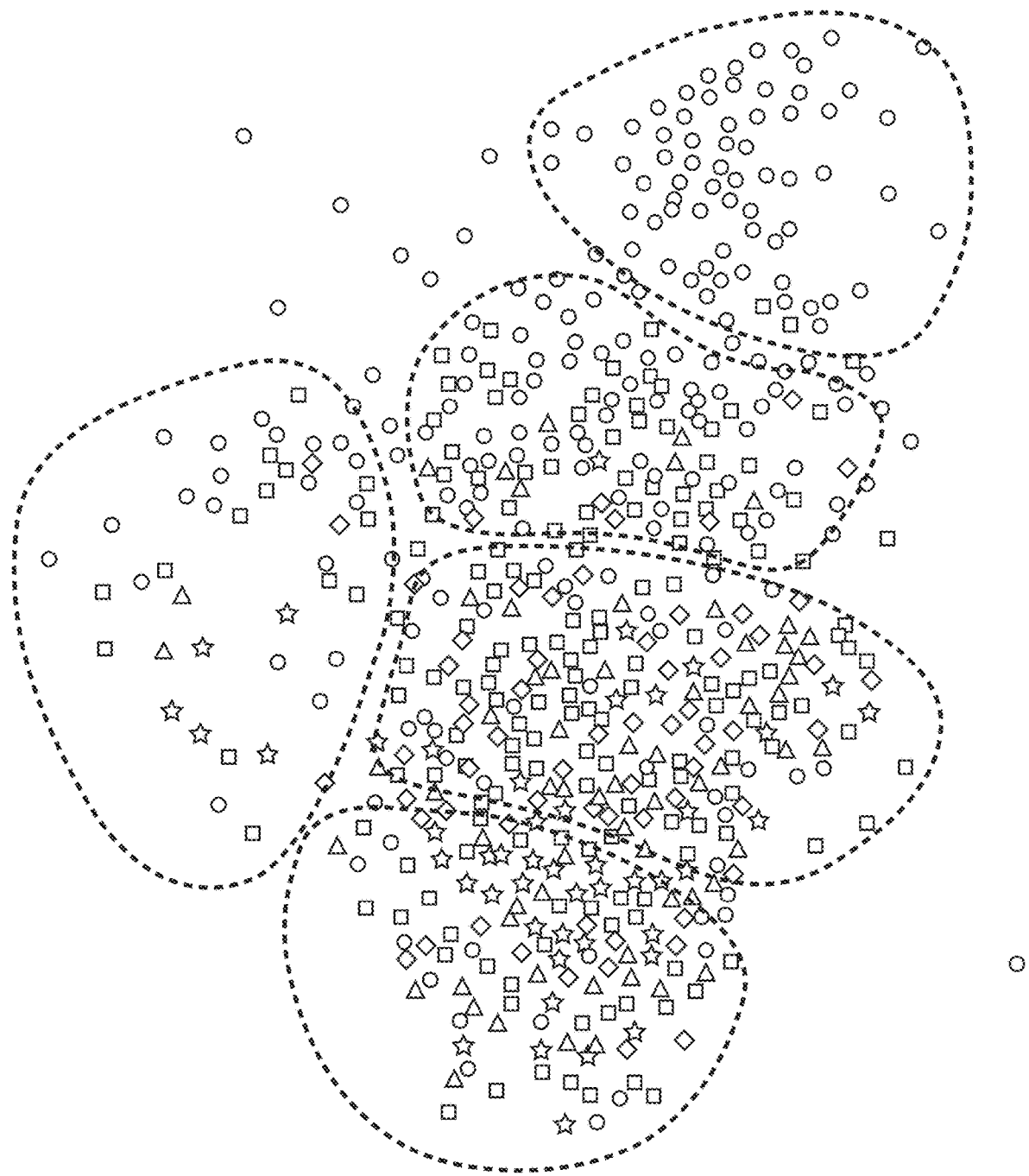
Figure 4E:
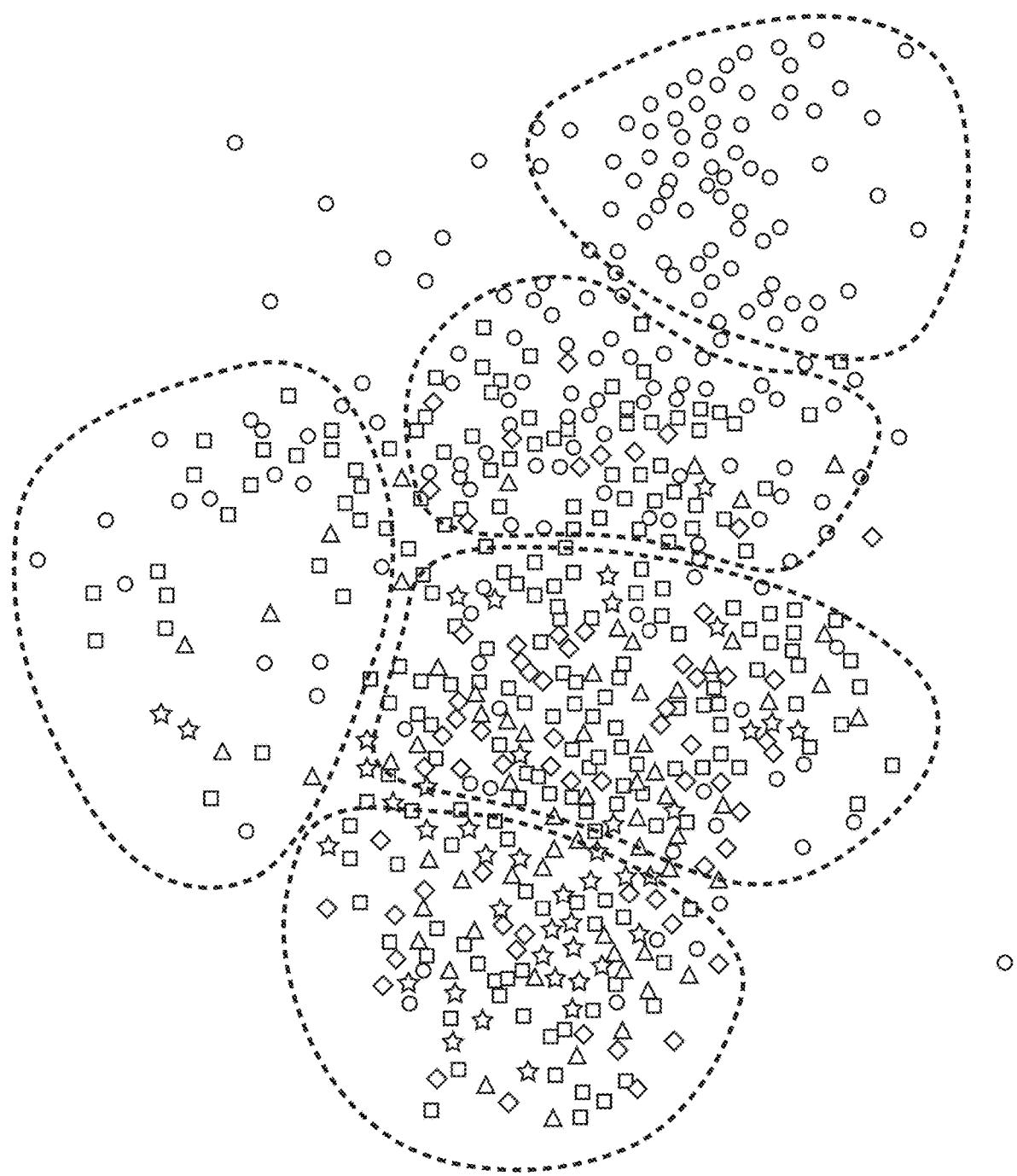
Figure 4F:
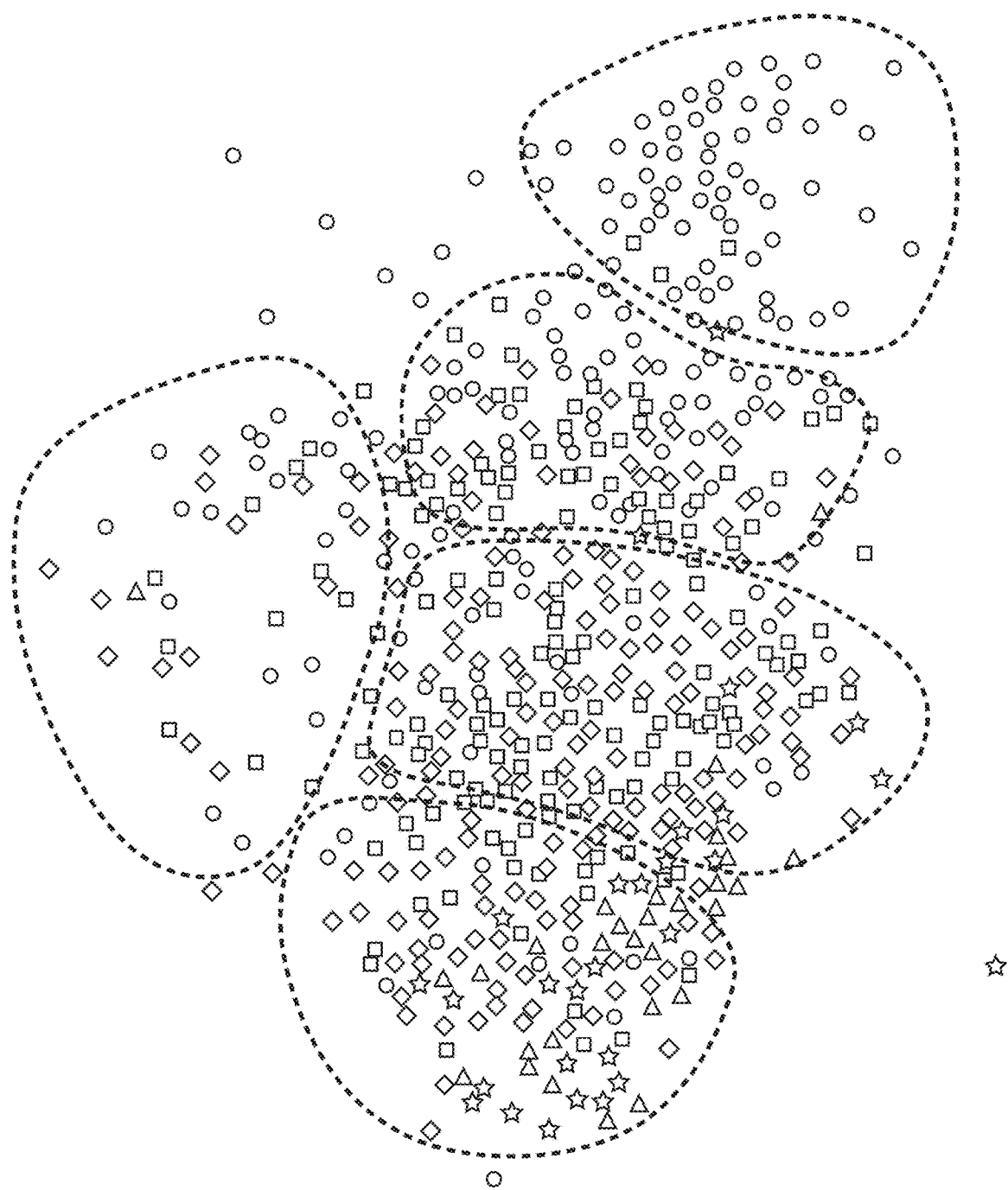
Figure 4G:
Figure 4H:
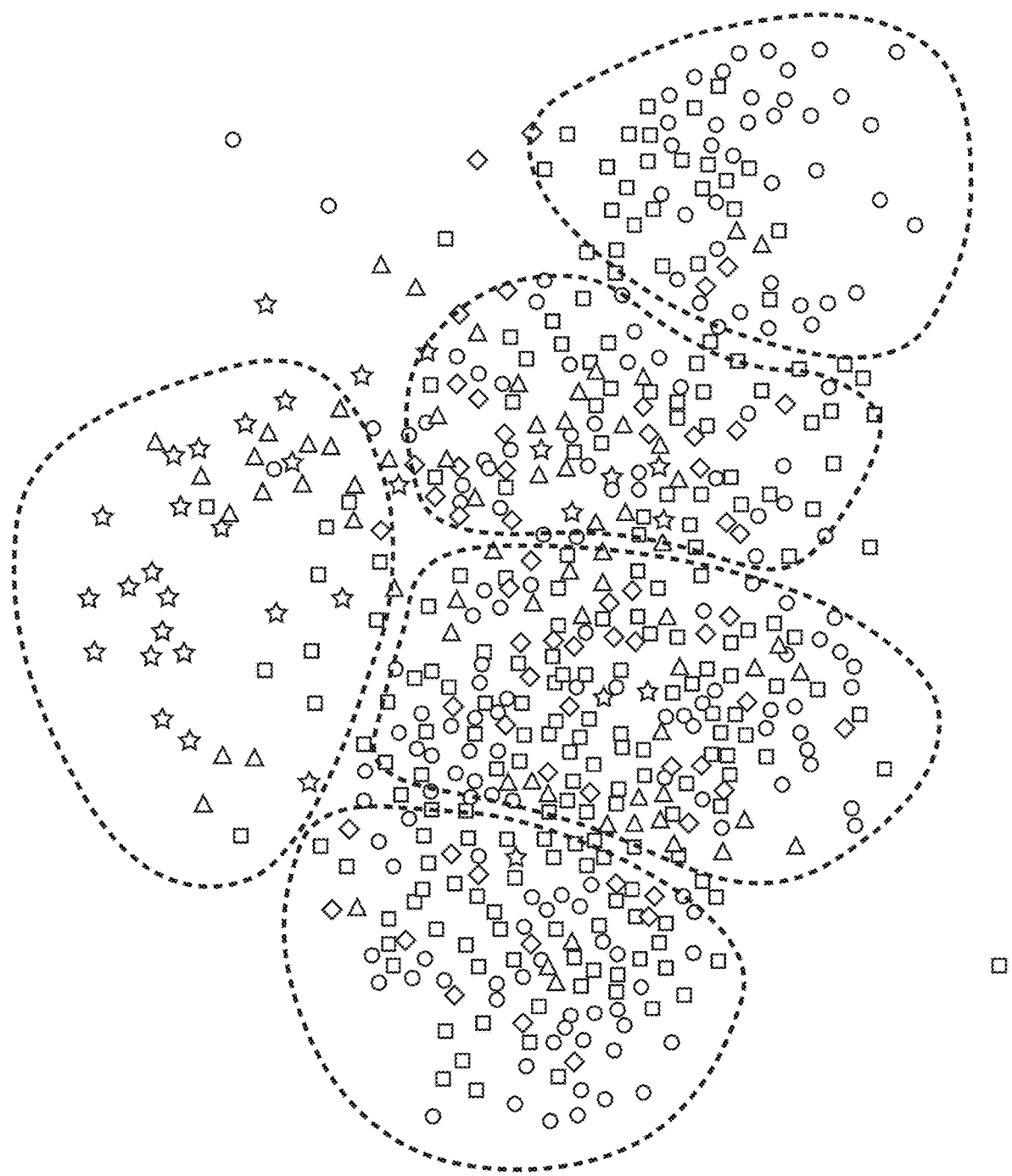
Figure 4I:
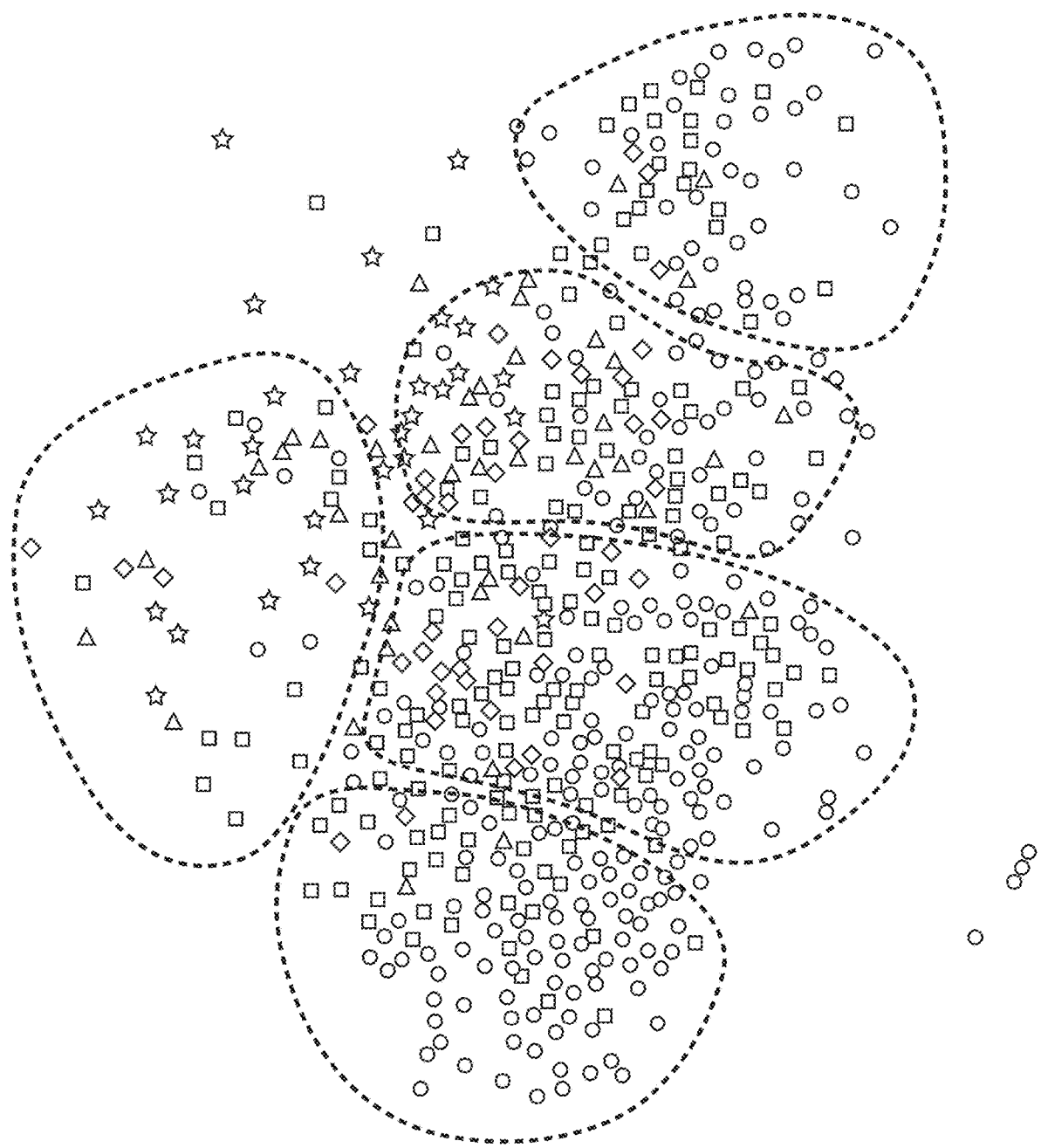
Figure 4J:
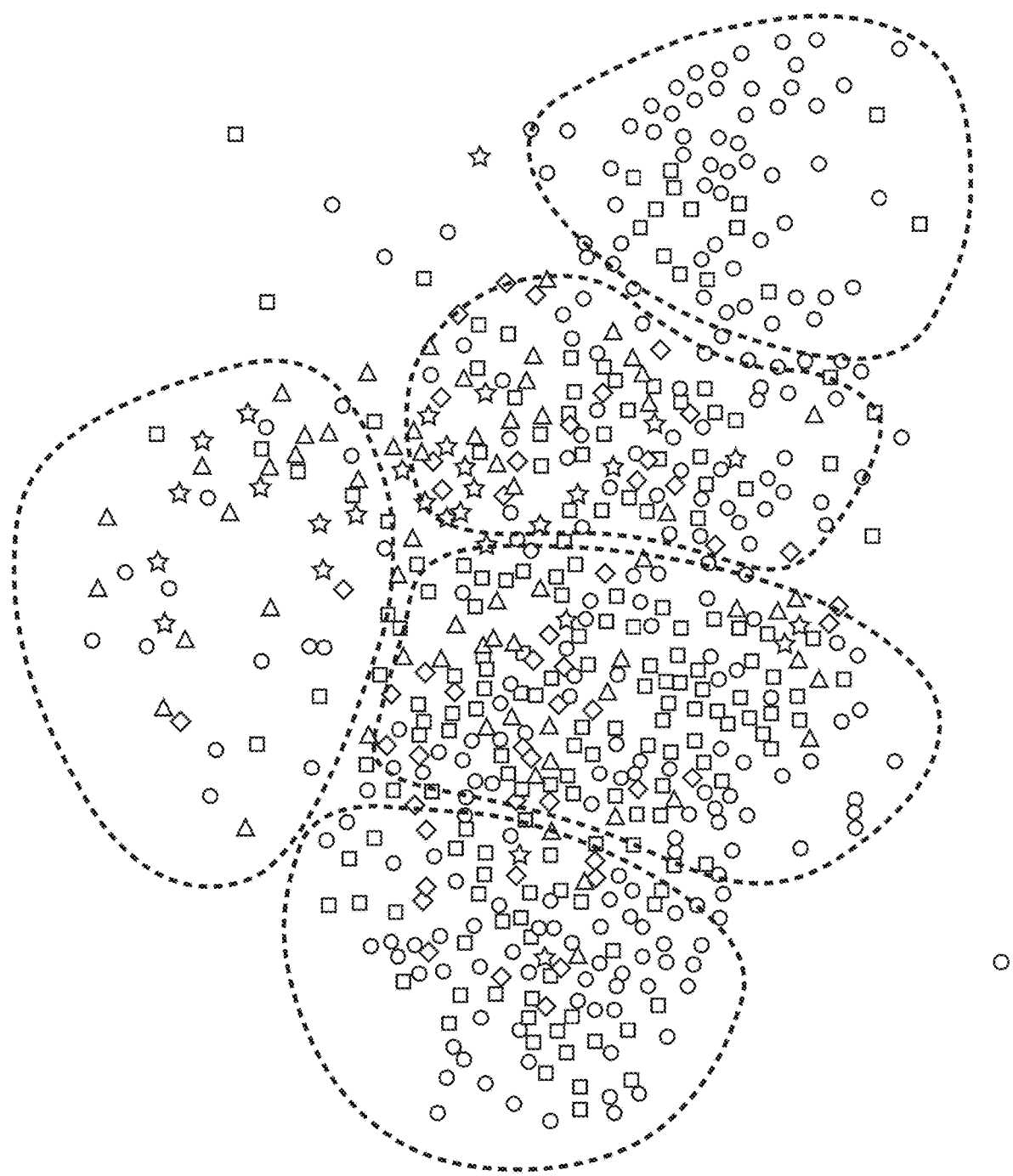

This simplified design allows utilizing the same complementarity/ligation sequence for many different mRNAs, only varying the target hybridization sequence. We implemented multiplexed imaging by iterative reannealing of fluorescent detection probes onto the same specimen. With this approach we have detected the expression of 24 genes in OVCAR4 cells (FIG. 3). We could equally detect highly expressed genes (ACTB, GAPDH) as well as low-expressed genes (CD24, E-cadherin). The imaging approach allowed us to characterize subcellular localization of RNA targets. While most RNAs were present exclusively in the cytoplasm, we found that mRNA of PBOV1, a human-specific protein coding gene that originated from a noncoding RNA less than 5 million years ago, exhibited preferential nuclear localization, suggesting a dual function as a coding and a non-coding RNA. To perform quantitative analysis of joint gene expression, images capturing 602 cells were segmented and converted into single-cell RNA expression vectors. Analysis of gene co-expression across single cells revealed a major co-expression group of proliferation-related genes that showed highly correlated expression (FIG. 4A).

Finally, individual cells were clustered and represented in force-directed layout, (see Samusik et al. (2016) Nature Methods 6:493-496 for methods). Cluster 1 was enriched in cells expressing WFDC2, Cluster 2 was positive for E-cadherin and MUC16, Cluster 3 expressed PBOV1, Clusters 4 and 5 exhibited proliferative phenotype, co-expressing cMyc, CD13 and Ki-67. Cluster 4 was positive for E-cadherin while Cluster 5 was negative for E-cadherin, but expressed MycN in addition to cMyc. This finding demonstrates a considerable degree of phenotypic diversity of OVCAR4 cells in this cell line.

Thus SNAIL-RCA enables an easily configured, efficiently managed, quantitative detection of gene expression levels in single cells.

Methods

Cell Culture. OVCAR4 cells were cultured in RPMI-1640 medium (Thermo Fisher Scientific) with 10% FBS (Thermo Fisher Scientific), 100 U/mL penicillin/100 µg/mL streptomycin (Thermo Fisher Scientific). Cells were fixed at 60% confluency by incubating with 1.6% formaldehyde solution in serum-free RPMI-1640 medium for 30 minutes at room temperature. Following that, the cells were transferred on ice and permeabilized with ice-cold methanol (Sigma Aldrich) and stored under methanol at −80 C.

SNAIL protocol. SNAIL probe sequences were designed using the SNAIL-designer software developed in-house, a total of 4 probe pairs per gene were designed. The probes were synthesized at the IDT and were shipped and stored in the IDTE buffer at 100 µM. The carrier solution for most of the protocol steps, including washes, was PBS, 0.1% Tween-20 (Sigma-Aldrich) and 4 U/mL RNasin. Cover slips with formaldehyde-fixed and methanol-permeabilized cells were washed with PBS, 0.1% Tween (Sigma-Aldrich) and 4 U/mL RNasin and 20 mM ribonucleoside vanadyl complex (New England BioLabs). Hybridizations with SNAIL probes were performed in a buffer based on DEPC-treated water (Thermo Fisher Scientific) containing 1× saline-sodium citrate (SSC) (Affymetrix), 2.5% vol/vol polyvinylsulfonic acid, 20 mM ribonucleoside vanadyl complex (New England BioLabs), 40 U/mL RNasin, 1% Tween-20, and 100 µg/mL salmon sperm DNA (Thermo Fisher Scientific). SNAIL probes for all target transcripts of an experiment were mixed and heated to 90° C. for 5 min. Probes were then mixed with the hybridization buffer at a final concentration of 200 nM and added to cells. Cells were incubated for 1 h at 40° C. and washed three times. Cells were then incubated for 20 min in a buffer containing PBS, 4×SSC and 40 U/mL RNasin at 40° C. After two washes, cells were incubated for 1 hour with Quick Ligase (New England Biolabs) at 37° C. and then for 2 hours with phi29 DNA polymerase (Thermo Fisher Scientific) at 30° C. under agitation. Longer amplification (up to 16 h) generally increases signal intensity. Both enzymes were used according to their respective manufacturers' instructions.

Imaging. Cell nuclei were stained with Hoechst 34580 (Thermo Fisher Scientific). RCA products were detected by annealing detection oligonucleotides conjugated to fluorescent dyes (ATTO-488, ATTO-595, ATTO-647). Cells were subject to cycles of annealing, imaging and stripping using custom-built fluidics setup and imaged with Keyence BZ-X710 microscope. Detection oligonucleotides, annealing and stripping buffers were provided by Akoya Biosciences Inc (San Francisco, USA).

What is claimed is:

1. A method for determining the level of a target nucleic acid in a fixed and permeabilized single cell, the method comprising:

contacting a fixed and permeabilized single cell with a pair of SNAIL oligonucleotide primers under conditions permissive for a specific hybridizations of the pair of SNAIL oligonucleotide primers to the target nucleic acid, wherein the pair of SNAIL oligonucleotide primers comprises a Splint Primer Oligonucleotide (SPO) and a Padlock Oligonucleotide (PO), wherein each of SPO and PO comprise a first complementarity region and the first complementarity region of the SPO and the first complementarity region of the PO are complementary to two adjacent sequences on the target nucleic acid, wherein the first complementarity region of the SPO is CR1 and the first complementarity region of the PO is CR1' and each of the SPO and the PO further comprises a second complementarity region, wherein the second complementarity region of the SPO is CR2 located adjacent to the CR1 and the second complementarity region of the PO is CR2' located adjacent to the CR1'; wherein the CR2' is a split region of the PO such that the 5' and the 3' ends of the PO hybridize to the CR2 and are positioned directly adjacent to one another after said contacting a fixed and permeabilized single cell with a pair of SNAIL oligonucleotide primers;

washing the cell to remove the pair of SNAIL oligonucleotide primers unbound to the target nucleic acid;

after the washing step, contacting the cell with a ligase such that the 5' and the 3' ends of the PO hybridized to the CR2 are ligated to each other and generating a closed circle;

performing in situ rolling circle amplification using the closed circle as a template and the SPO as a primer and generating an amplification product in situ;

contacting the amplification product in situ with a nucleic acid detection probe labeled with one or more of a fluorophore, an isotope, or a mass tag under conditions permissive for a specific hybridization of the detection probe to the amplification product and generating a labeled cell; and determining the level of the target nucleic acid in the fixed and permeabilized single cell by detecting the level of the detection probe bound to the amplification product in the labeled cell and subjecting the labeled cell to an analysis performed by mass cytometry or fluorescence-activated flow cytometry.

2. The method of claim 1, wherein the SNAIL oligonucleotide primer pairs are denatured by heating before said contacting a fixed and permeabilized single cell with a pair of SNAIL oligonucleotide primers.

3. The method of claim 1, wherein the cell is present in a population of cells.

4. The method of claim 3, wherein the cell population comprises a plurality of cell types.

5. The method of claim 1, wherein the target nucleic acid is RNA.

6. The method of claim 5, wherein the RNA is mRNA.

7. The method of claim 1, wherein the target nucleic acid is DNA.

8. The method of claim 1, further comprising: contacting the labeled cell with one or more marker detection reagents that specifically bind to one or more non-nucleic acid markers, determining the levels of the one or more marker detection reagents bound to the labeled cell, and profiling the levels of the one or more non-nucleic acid markers in the fixed and permeabilized single cell.

9. The method of claim 8, wherein the one or more non-nucleic acid markers are protein markers.

10. The method of claim 1, wherein the sequences of the pair of SNAIL oligonucleotide primers further comprises a detection barcode sequence for identification of the target nucleic acid.

11. The method of claim 1, wherein the detection probe is removed from the amplification product after the detecting and subjecting step.

12. A method for determining the level of a target nucleic acid from different nucleic acids in a fixed and permeabilized single cell, the method comprising:

contacting a fixed and permeabilized single cell with a plurality of pairs of SNAIL oligonucleotide primers having specificity for different target nucleic acids under conditions permissive for a specific hybridization of the plurality of pairs of SNAIL oligonucleotide primers to the different target nucleic acids, wherein each pair of the plurality of pairs of SNAIL oligonucleotide primers comprises a Splint Primer Oligonucleotide (SPO) and a Padlock Oligonucleotide (PO), wherein each of the SPO and the PO of each pair of the plurality of pairs of SNAIL oligonucleotide primers comprises a first complementarity region and the first complementarity region of the SPO and the first complementarity region of the PO of each pair of the plurality of pairs of SNAIL oligonucleotide are complementary to two adjacent sequences on one of the different target nucleic acids, wherein the first complementarity region of the SPO of each pair of the plurality of pairs of SNAIL oligonucleotide is CR1 and the first complementarity region of the PO of each pair of the plurality of pairs of SNAIL oligonucleotide is CR1'; and each of the SPO and the PO of each pair of the plurality of pairs of SNAIL oligonucleotide further comprises a second complementarity region, wherein the second complementarity region of the SPO of each pair of the plurality of pairs of SNAIL oligonucleotide is CR2 and the CR1 and the CR2 of the SPO of each pair of the plurality of pairs of SNAIL oligonucleotide are located adjacent to one another and the second complementarity region of the PO of each pair of the plurality of pairs of SNAIL oligonucleotide is CR2' and the CR1' and the CR2' of the PO of each pair of the plurality of pairs of SNAIL oligonucleotide are located adjacent to one another; wherein the CR2' is a split region of the PO of each pair of the plurality of pairs of SNAIL oligonucleotide such that the 5' and the 3' ends of the PO of one pair of the plurality of pairs of SNAIL oligonucleotide hybridize to the CR2 of the SPO of the one pair of the plurality of pairs of SNAIL oligonucleotide and are positioned directly adjacent to one another after said contacting a fixed and permeabilized single cell with a plurality of SNAIL oligonucleotide primers;

washing the cell to remove the plurality of pairs of SNAIL oligonucleotide primers unbound to the different target nucleic acids;

after the washing step, contacting the cell with a ligase such that the 5' and the 3' ends of the PO of the one pair of the plurality of pairs of SNAIL oligonucleotide hybridized to the CR2 of the SPO of the one pair of the plurality of pairs of SNAIL oligonucleotide are ligated to each other and generating a closed circle;

performing rolling circle amplifications in situ using the closed circle as a template and the SPO of the one pair of the plurality of pairs of SNAIL oligonucleotide as a primer and generating an amplification product in situ;

contacting the amplification product in situ with a nucleic acid detection probe labeled with one or more of a fluorophore, an isotope, or a mass tag under conditions permissive for a specific hybridization of the detection probe to the amplification product and generating a labeled cell; and determining the level of the target nucleic acid from the different nucleic acids in the fixed and permeabilized single cell by determining the level of the detection probe bound to the amplification product in the labeled cell and subjecting the labeled cell to an analysis performed by mass cytometry or fluorescence-activated flow cytometry.

13. The method of claim 12, wherein the plurality of pairs of SNAIL oligonucleotide primers are specific for at least 5 of the different target nucleic acids.

14. The method of claim 12, wherein the different target nucleic acids are RNAs.

* * * * *

SEQUENCE LISTING

<160> NUMBER OF SEQ ID NOS: 5

<210> SEQ ID NO 1
<211> LENGTH: 35
<212> TYPE: DNA
<213> ORGANISM: Artificial Sequence
<220> FEATURE:
<223> OTHER INFORMATION: Generated oligonucleotide based on molecule to
      be detected.

<400> SEQUENCE: 1
ctcatcagca cagctatgat gataatgttt atctt                              35

<210> SEQ ID NO 2
<211> LENGTH: 59
<212> TYPE: DNA
<213> ORGANISM: Artificial sequence
<220> FEATURE:
<223> OTHER INFORMATION: Generated oligonucleotide based on molecule to
      be detected.

<400> SEQUENCE: 2
aacattaaaa tcctagcaca gggactcgcg aattaaagtc ttagagagag agagaagat    59

<210> SEQ ID NO 3
<211> LENGTH: 70
<212> TYPE: DNA
<213> ORGANISM: Homo sapiens

<400> SEQUENCE: 3
atggccataa gtggagtccc tgtgctagga tttttcatca tagctgtgct gatgagcgct  60
caggaatcat                                                         70

<210> SEQ ID NO 4
<211> LENGTH: 168
<212> TYPE: DNA
<213> ORGANISM: Artificial sequence
<220> FEATURE:
<223> OTHER INFORMATION: Generated oligonucleotide based on molecule to
      be detected.

<400> SEQUENCE: 4
ctcatcagca cagctatgat gataatgtta tccgcttcct ctctctctaa agacttaatc  60
gcgcccctgt gctaggataa tgtttatctt gcctctctct ctaagactta atcgcgagtc 120
aatgtgctag gataatgttt atcttctctc tctctctaac tctctctc              168

<210> SEQ ID NO 5
<211> LENGTH: 90
<212> TYPE: DNA
<213> ORGANISM: Artificial sequence
<220> FEATURE:
<223> OTHER INFORMATION: Generated oligonucleotide based on molecule to
      be detected.

<400> SEQUENCE: 5
tctcccctgt gctaggataa tctttatctt ctctctctct ctaagactta atcgcgagtc  60
ccctgtgcta ggagataatg tttatcttta                                   90